US011061240B2

(12) United States Patent
Godar et al.

(10) Patent No.: US 11,061,240 B2
(45) Date of Patent: Jul. 13, 2021

(54) HEAD-MOUNTABLE APPARATUS AND METHODS

(71) Applicant: Sony Interactive Entertainment Inc., Tokyo (JP)

(72) Inventors: Anthony William Godar, London (GB); Richard James Forster, London (GB)

(73) Assignee: Sony Interactive Entertainment Inc., Tokyo (JP)

( * ) Notice: Subject to any disclaimer, the term of this patent is extended or adjusted under 35 U.S.C. 154(b) by 0 days.

(21) Appl. No.: 16/636,446

(22) PCT Filed: Jul. 13, 2018

(86) PCT No.: PCT/GB2018/051998
§ 371 (c)(1),
(2) Date: Feb. 4, 2020

(87) PCT Pub. No.: WO2019/030467
PCT Pub. Date: Feb. 14, 2019

(65) Prior Publication Data
US 2020/0174262 A1    Jun. 4, 2020

(30) Foreign Application Priority Data
Aug. 8, 2017 (GB) ..................... 1712690

(51) Int. Cl.
*G02B 27/01* (2006.01)
*A61B 5/00* (2006.01)
(Continued)

(52) U.S. Cl.
CPC ...... *G02B 27/0179* (2013.01); *A61B 5/02438* (2013.01); *A61B 5/0531* (2013.01);
(Continued)

(58) Field of Classification Search
CPC ....... A61B 5/165; A61B 5/6803; A61B 5/163; A61B 5/6814; A61B 5/02438;
(Continued)

(56) References Cited

U.S. PATENT DOCUMENTS 6,525,732 B1 * 2/2003 Gadh ..................... G06T 15/20
345/428
2013/0083062 A1   4/2013 Geisner
(Continued)

FOREIGN PATENT DOCUMENTS

CN    105607259 A    5/2016
EP    2919098 A1    9/2015
(Continued)

OTHER PUBLICATIONS

International Search Report and Written Opinion on Patentability for corresponding PCT Application No. PCT/GB2018/051998, 15 pages, dated Aug. 27, 2018.
(Continued)

*Primary Examiner* — Dong Hui Liang
(74) *Attorney, Agent, or Firm* — Matthew B. Dernier, Esq.

(57) ABSTRACT

A method of adapting content responsive to a well-being of a user wearing a head mountable display (HMD) includes detecting, by one or more sensors, one or more parameters indicating one or more current properties of the user wearing the HMD, generating information indicating the well-being of the user based on the one or more parameters, and adapting an output of the HMD responsive to the generated information, the output comprising at least one of an image and an audio signal.

22 Claims, 19 Drawing Sheets

(51) Int. Cl.

| | | |
|---|---|---|
| *A61B 5/024* | (2006.01) | |
| *A61B 5/053* | (2021.01) | |
| *G02B 27/00* | (2006.01) | |
| *G06F 3/01* | (2006.01) | |
| *A61B 5/0531* | (2021.01) | |
| *H04N 13/268* | (2018.01) | |
| *H04N 13/25* | (2018.01) | |
| *H04N 13/275* | (2018.01) | |
| *G06K 9/32* | (2006.01) | |
| *G06T 15/04* | (2011.01) | |
| *G06T 15/20* | (2011.01) | |

(52) U.S. Cl.
CPC ........ *A61B 5/6803* (2013.01); *G02B 27/0093* (2013.01); *G02B 27/0172* (2013.01); *G06F 3/013* (2013.01); *G06F 3/015* (2013.01); *G06K 9/3233* (2013.01); *G06T 15/04* (2013.01); *G06T 15/205* (2013.01); *H04N 13/25* (2018.05); *H04N 13/268* (2018.05); *H04N 13/275* (2018.05); *G02B 2027/0178* (2013.01); *G02B 2027/0187* (2013.01)

(58) Field of Classification Search
CPC ..... A61B 5/0816; A61B 5/0476; G06F 3/011; G06F 3/015; G06F 3/012; G06F 3/013; G06F 3/04815; G06F 1/163; G06F 2203/011; G02B 27/017; G02B 2027/0178
See application file for complete search history.

(56) References Cited

U.S. PATENT DOCUMENTS

| | | | | |
|---|---|---|---|---|
| 2013/0178257 A1* | 7/2013 | Langseth | ............... | A63F 13/812 463/4 |
| 2014/0064557 A1* | 3/2014 | Hara | ....................... | G06F 3/012 382/103 |
| 2014/0139551 A1* | 5/2014 | McCulloch | ............. | G09G 5/377 345/633 |
| 2014/0268356 A1* | 9/2014 | Bolas | ................... | G02B 27/017 359/630 |
| 2015/0153570 A1* | 6/2015 | Yamamoto | ........ | H04M 1/72448 345/184 |
| 2016/0077547 A1* | 3/2016 | Aimone | ............... | A61B 5/0006 345/8 |
| 2016/0109851 A1* | 4/2016 | Tsang | ..................... | G06F 1/163 359/9 |
| 2016/0178904 A1* | 6/2016 | Deleeuw | ................. | G06F 3/011 345/8 |
| 2017/0168568 A1 | 6/2017 | Petrov | | |
| 2017/0178052 A1* | 6/2017 | Durham | ........... | G06Q 10/06311 |
| 2017/0255262 A1 | 9/2017 | Liu | | |
| 2017/0293356 A1* | 10/2017 | Khaderi | ................... | G06F 3/147 |
| 2017/0358141 A1* | 12/2017 | Stafford | ................ | A63F 13/537 |
| 2018/0075764 A1* | 3/2018 | Bachani | ............... | A61B 5/0205 |
| 2018/0113509 A1* | 4/2018 | Kim | ........................ | H04W 4/38 |
| 2018/0271383 A1 | 9/2018 | Lee | | |

FOREIGN PATENT DOCUMENTS

| | | |
|---|---|---|
| EP | 3035681 A1 | 6/2016 |
| GB | 2494907 A | 3/2013 |
| KR | 20160074156 A | 6/2016 |
| KR | 1020170055135 A | 5/2017 |
| WO | 2015030797 A1 | 3/2015 |
| WO | 2016126522 A1 | 8/2016 |

OTHER PUBLICATIONS

Combined Search and Examination Report for corresponding GB Application No. 1712690.5, 8 pages, dated Jan. 17, 2018.

* cited by examiner

LEFT RIGHT

2010

2020

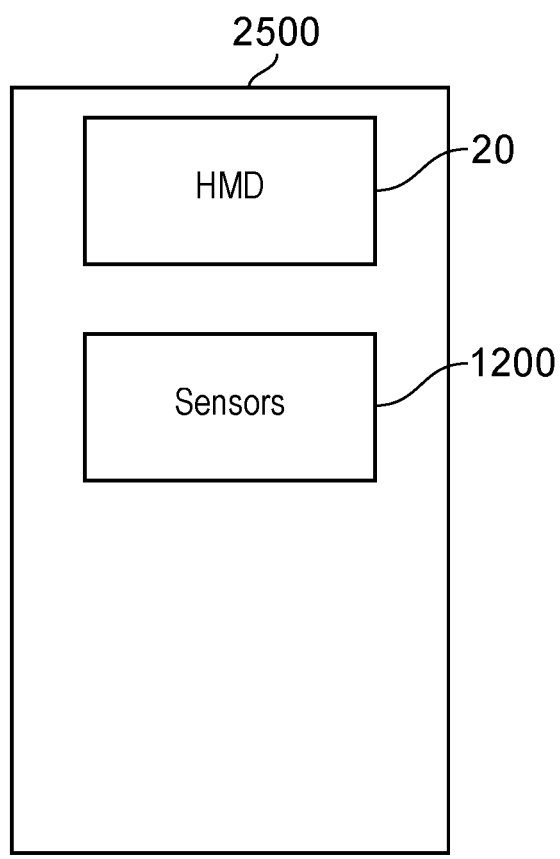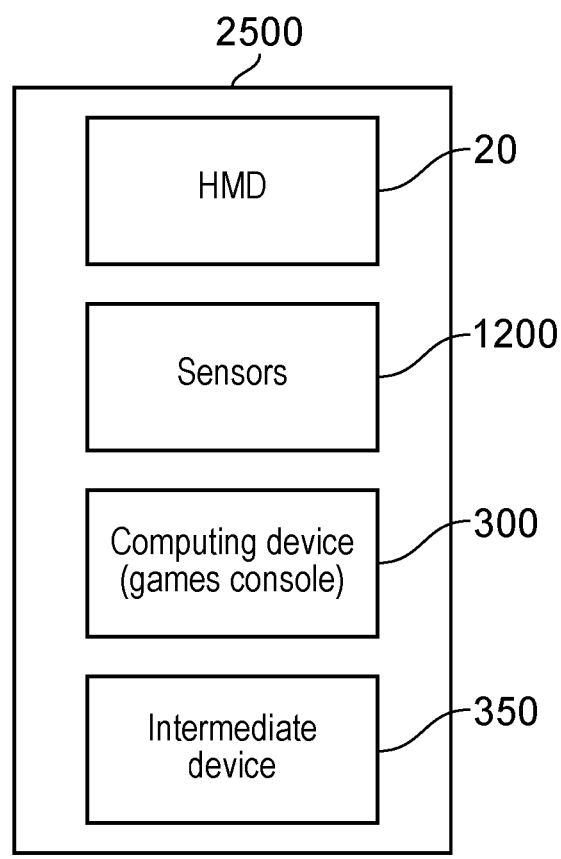
FIG. 25a
FIG. 25b

HEAD-MOUNTABLE APPARATUS AND METHODS

BACKGROUND

Field of the Disclosure

This disclosure relates to virtual reality apparatus and methods.

Description of the Prior Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present disclosure.

A head-mountable display (HMD) is one example of a head-mountable apparatus for use in a virtual reality system in which an HMD wearer views a virtual environment. In an HMD, an image or video display device is provided which may be worn on the head or as part of a helmet. Either one eye or both eyes are provided with small electronic display devices.

Although the original development of HMDs and virtual reality was perhaps driven by the military and professional applications of these devices, HMDs are becoming more popular for use by casual users in, for example, computer game or domestic computing applications.

The techniques to be discussed are applicable to individual three-dimensional images or to video signals comprising successive three-dimensional images. Therefore, references to "images" in the discussion below should be taken to encompass the use of the same techniques in respect of video signals.

The foregoing paragraphs have been provided by way of general introduction, and are not intended to limit the scope of the following claims. The described embodiments, together with further advantages, will be best understood by reference to the following detailed description taken in conjunction with the accompanying drawings.

SUMMARY

An example embodiment provides a method of adapting content responsive to a well-being of a user wearing an HMD, the method comprising the steps of:

detecting, by one or more sensors, one or more parameters indicating one or more current properties of the user wearing the HMD;

generating information indicating the well-being of the user based on the one or more parameters; and adapting an output of the HMD responsive to the generated information, the output comprising at least one of an image and an audio signal.

Another example embodiment provides an apparatus for adapting content responsive to a well-being of a user wearing an HMD, the apparatus comprising:

one or more sensors configured to detect one or more parameters indicating one or more current properties of the user wearing the HMD;

a processor configured to generate information indicating the well-being of the user based on the one or more parameters; and an HMD configured to output at least one of an image and an audio signal, the output adapted responsive to the generated information.

Another example embodiment provides computer software which, when executed by a computer, causes the computer to perform the steps of the method defined above.

Example embodiments provide a machine-readable, non-transitory storage medium which stores such computer software.

Various other aspects and features of the present disclosure are defined in the appended claims and within the text of the accompanying description and include at least a head mountable apparatus such as a display and a method of operating a head-mountable apparatus as well as a computer program.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 25a schematically illustrates an apparatus for updating content responsive to a well-being of a user wearing an HMD comprising an HMD and one or more sensors;

FIG. 25b schematically illustrates an apparatus for updating content responsive to a well-being of a user wearing an HMD comprising an HMD, one or more sensors, a computing device and an intermediate device.

DESCRIPTION OF THE EMBODIMENTS

Figure 1:
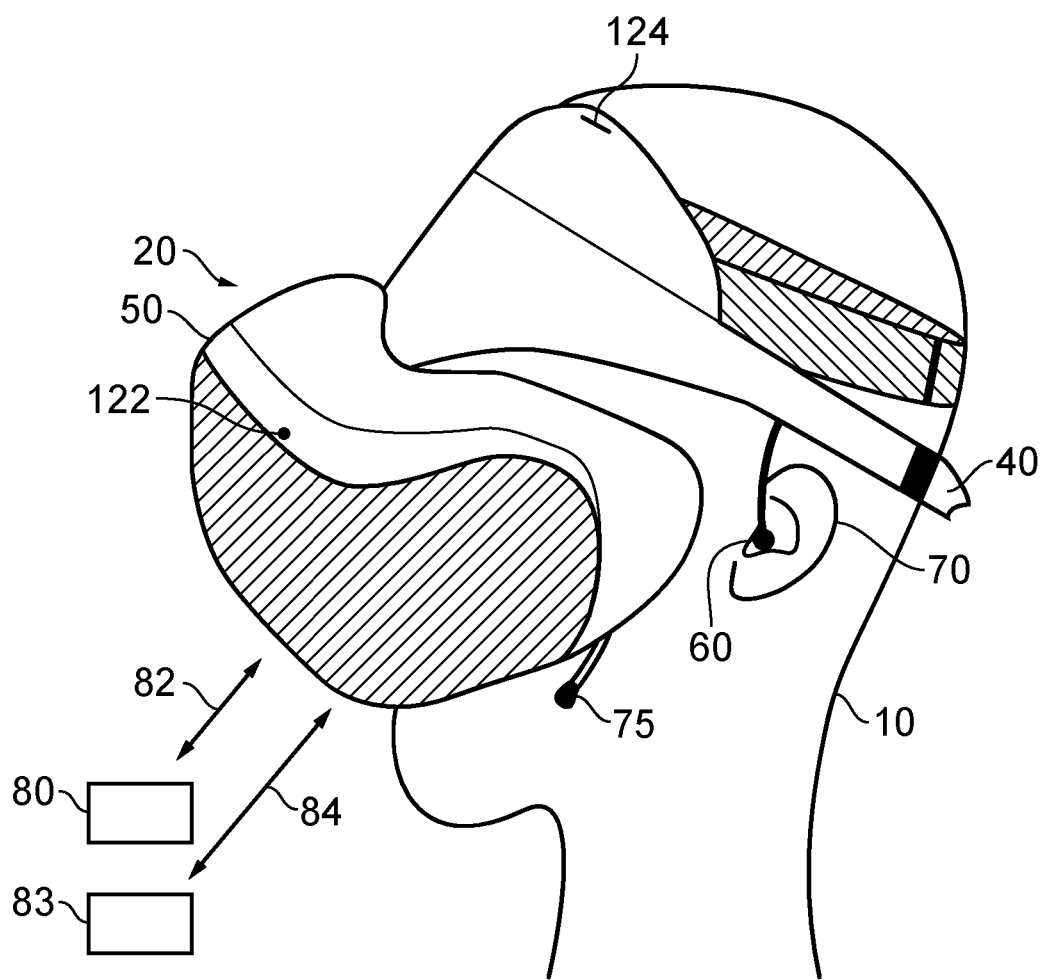
FIG. 1 schematically illustrates an HMD worn by a user.

Referring now to FIG. 1, a user 10 is wearing an HMD 20 (as an example of a generic head-mountable apparatus or virtual reality apparatus). The HMD comprises a frame 40, in this example formed of a rear strap and a top strap, and a display portion 50.

Note that the HMD of FIG. 1 may comprise further features, to be described below in connection with other drawings, but which are not shown in FIG. 1 for clarity of this initial explanation.

The HMD of FIG. 1 completely (or at least substantially completely) obscures the user's view of the surrounding environment. All that the user can see is the pair of images displayed within the HMD.

The HMD has associated headphone audio transducers or earpieces 60 which fit into the user's left and right ears 70. The earpieces 60 replay an audio signal provided from an external source, which may be the same as the video signal source which provides the video signal for display to the user's eyes. A boom microphone 75 is mounted on the HMD so as to extend towards the user's mouth.

The combination of the fact that the user can see only what is displayed by the HMD and, subject to the limitations of the noise blocking or active cancellation properties of the earpieces and associated electronics, can hear only what is provided via the earpieces, mean that this HMD may be considered as a so-called "full immersion" HMD. Note however that in some embodiments the HMD is not a full immersion HMD, and may provide at least some facility for the user to see and/or hear the user's surroundings. This could be by providing some degree of transparency or partial transparency in the display arrangements, and/or by projecting a view of the outside (captured using a camera, for example a camera mounted on the HMD) via the HMD's displays, and/or by allowing the transmission of ambient sound past the earpieces and/or by providing a microphone to generate an input sound signal (for transmission to the earpieces) dependent upon the ambient sound.

A front-facing camera 122 may capture images to the front of the HMD, in use. A Bluetooth® antenna 124 may provide communication facilities or may simply be arranged as a directional antenna to allow a detection of the direction of a nearby Bluetooth® transmitter.

In operation, a video signal is provided for display by the HMD. This could be provided by an external video signal source 80 such as a video games machine or data processing apparatus (such as a personal computer), in which case the signals could be transmitted to the HMD by a wired or a wireless connection 82. Examples of suitable wireless connections include Bluetooth® connections. Audio signals for the earpieces 60 can be carried by the same connection. Similarly, any control signals passed from the HMD to the video (audio) signal source may be carried by the same connection. Furthermore, a power supply 83 (including one or more batteries and/or being connectable to a mains power outlet) may be linked by a cable 84 to the HMD. Note that the power supply 83 and the video signal source 80 may be separate units or may be embodied as the same physical unit. There may be separate cables for power and video (and indeed for audio) signal supply, or these may be combined for carriage on a single cable (for example, using separate conductors, as in a USB cable, or in a similar way to a "power over Ethernet" arrangement in which data is carried as a balanced signal and power as direct current, over the same collection of physical wires). The video and/or audio signal may be carried by, for example, an optical fibre cable. In other embodiments, at least part of the functionality associated with generating image and/or audio signals for presentation to the user may be carried out by circuitry and/or processing forming part of the HMD itself. A power supply may be provided as part of the HMD itself.

Some embodiments of the disclosure are applicable to an HMD having at least one electrical and/or optical cable linking the HMD to another device, such as a power supply and/or a video (and/or audio) signal source. So, embodiments of the disclosure can include, for example:

(a) an HMD having its own power supply (as part of the HMD arrangement) but a cabled connection to a video and/or audio signal source;

(b) an HMD having a cabled connection to a power supply and to a video and/or audio signal source, embodied as a single physical cable or more than one physical cable;

(c) an HMD having its own video and/or audio signal source (as part of the HMD arrangement) and a cabled connection to a power supply;

(d) an HMD having a wireless connection to a video and/or audio signal source and a cabled connection to a power supply; or (e) an HMD having its own video and/or audio signal source and its own power supply (both as part of the HMD arrangement).

If one or more cables are used, the physical position at which the cable 82 and/or 84 enters or joins the HMD is not particularly important from a technical point of view. Aesthetically, and to avoid the cable(s) brushing the user's face in operation, it would normally be the case that the cable(s) would enter or join the HMD at the side or back of the HMD (relative to the orientation of the user's head when worn in normal operation). Accordingly, the position of the cables 82, 84 relative to the HMD in FIG. 1 should be treated merely as a schematic representation.

Accordingly, the arrangement of FIG. 1 provides an example of a head-mountable display system comprising a frame to be mounted onto an observer's head, the frame defining one or two eye display positions which, in use, are positioned in front of a respective eye of the observer and a display element mounted with respect to each of the eye display positions, the display element providing a virtual image of a video display of a video signal from a video signal source to that eye of the observer.

FIG. 1 shows just one example of an HMD. Other formats are possible: for example an HMD could use a frame more similar to that associated with conventional eyeglasses, namely a substantially horizontal leg extending back from the display portion to the top rear of the user's ear, possibly curling down behind the ear. In other (not full immersion) examples, the user's view of the external environment may not in fact be entirely obscured; the displayed images could be arranged so as to be superposed (from the user's point of view) over the external environment. An example of such an arrangement will be described below with reference to FIG. 4.

In the example of FIG. 1, a separate respective display is provided for each of the user's eyes. A schematic plan view of how this is achieved is provided as FIG. 2, which illustrates the positions 100 of the user's eyes and the relative position 110 of the user's nose. The display portion 50, in schematic form, comprises an exterior shield 120 to mask ambient light from the user's eyes and an internal shield 130 which prevents one eye from seeing the display intended for the other eye. The combination of the user's face, the exterior shield 120 and the interior shield 130 form two compartments 140, one for each eye. In each of the compartments there is provided a display element 150 and one or more optical elements 160. The way in which the display element and the optical element(s) cooperate to provide a display to the user will be described with reference to FIG. 3.

Figure 3:
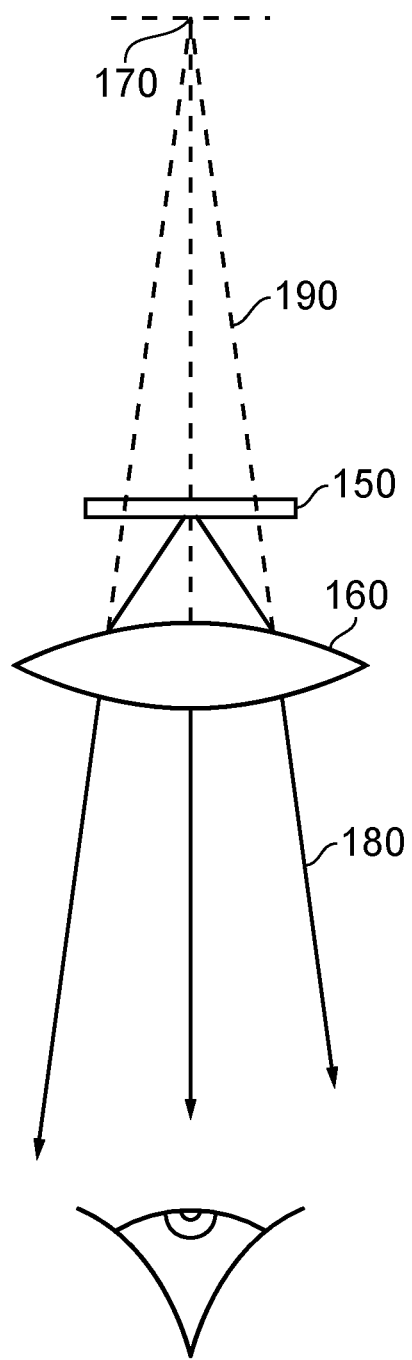
FIG. 3 schematically illustrates the formation of a virtual image by an HMD.

Referring to FIG. 3, the display element 150 generates a displayed image which is (in this example) refracted by the optical elements 160 (shown schematically as a convex lens but which could include compound lenses or other elements) so as to generate a virtual image 170 which appears to the user to be larger than and significantly further away than the real image generated by the display element 150. As an example, the virtual image may have an apparent image size (image diagonal) of more than 1 m and may be disposed at a distance of more than 1 m from the user's eye (or from the frame of the HMD). In general terms, depending on the purpose of the HMD, it is desirable to have the virtual image disposed a significant distance from the user. For example, if the HMD is for viewing movies or the like, it is desirable that the user's eyes are relaxed during such viewing, which requires a distance (to the virtual image) of at least several metres. In FIG. 3, solid lines (such as the line 180) are used to denote real optical rays, whereas broken lines (such as the line 190) are used to denote virtual rays.

Figure 4:
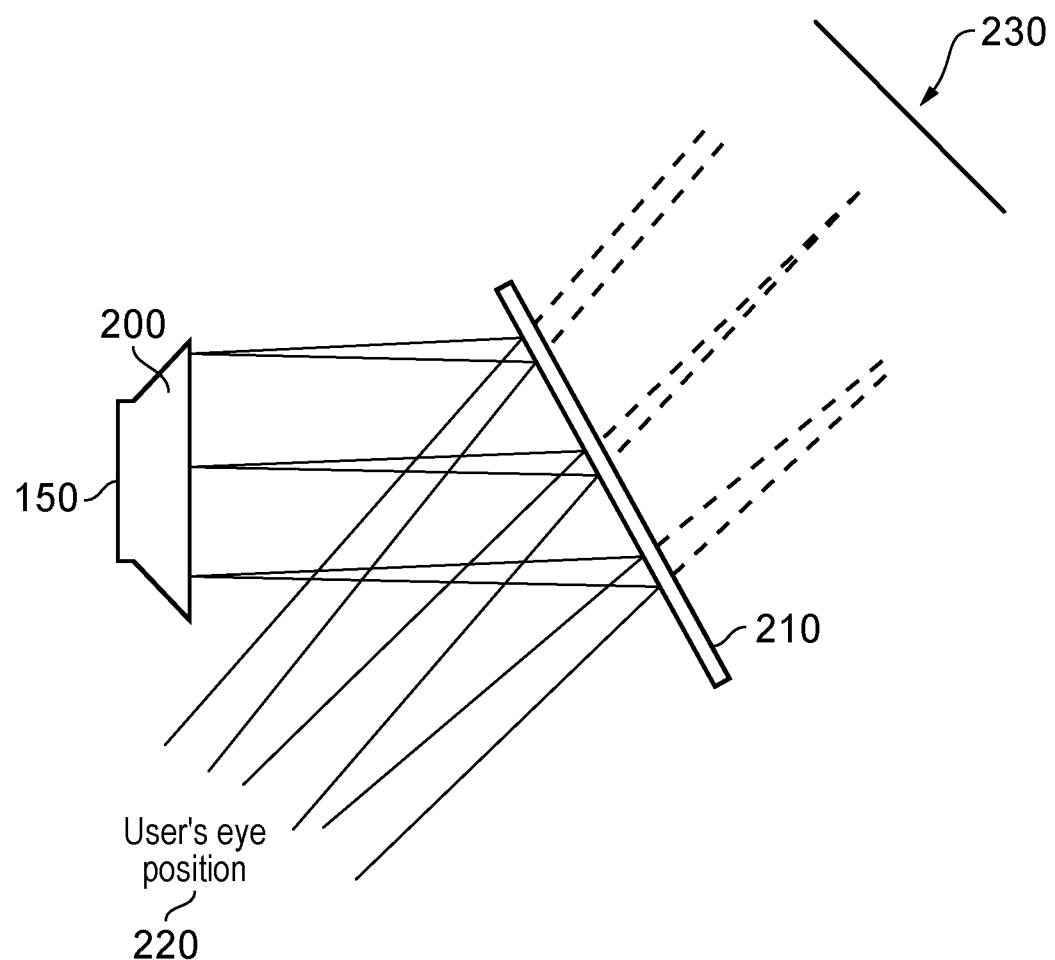
FIG. 4 schematically illustrates another type of display for use in an HMD.

An alternative arrangement is shown in FIG. 4. This arrangement may be used where it is desired that the user's view of the external environment is not entirely obscured. However, it is also applicable to HMDs in which the user's external view is wholly obscured. In the arrangement of FIG. 4, the display element 150 and optical elements 200 cooperate to provide an image which is projected onto a mirror 210, which deflects the image towards the user's eye position 220. The user perceives a virtual image to be located at a position 230 which is in front of the user and at a suitable distance from the user.

In the case of an HMD in which the user's view of the external surroundings is entirely obscured, the mirror 210 can be a substantially 100% reflective mirror. The arrangement of FIG. 4 then has the advantage that the display element and optical elements can be located closer to the centre of gravity of the user's head and to the side of the user's eyes, which can produce a less bulky HMD for the user to wear. Alternatively, if the HMD is designed not to completely obscure the user's view of the external environment, the mirror 210 can be made partially reflective so that the user sees the external environment, through the mirror 210, with the virtual image superposed over the real external environment.

Figure 5:
FIG. 5 schematically illustrates a pair of stereoscopic images.

In the case where separate respective displays are provided for each of the user's eyes, it is possible to display stereoscopic images. An example of a pair of stereoscopic images for display to the left and right eyes is shown in FIG. 5. The images exhibit a lateral displacement relative to one another, with the displacement of image features depending upon the (real or simulated) lateral separation of the cameras by which the images were captured, the angular convergence of the cameras and the (real or simulated) distance of each image feature from the camera position.

Note that the lateral displacements in FIG. 5 could in fact be the other way round, which is to say that the left eye image as drawn could in fact be the right eye image, and the right eye image as drawn could in fact be the left eye image. This is because some stereoscopic displays tend to shift objects to the right in the right eye image and to the left in the left eye image, so as to simulate the idea that the user is looking through a stereoscopic window onto the scene beyond. However, some HMDs use the arrangement shown in FIG. 5 because this gives the impression to the user that the user is viewing the scene through a pair of binoculars. The choice between these two arrangements is at the discretion of the system designer.

In some situations, an HMD may be used simply to view movies and the like. In this case, there is no change required to the apparent viewpoint of the displayed images as the user turns the user's head, for example from side to side. In other uses, however, such as those associated with virtual reality (VR) or augmented reality (AR) systems, the user's viewpoint needs to track movements with respect to a real or virtual space in which the user is located.

Figure 6:
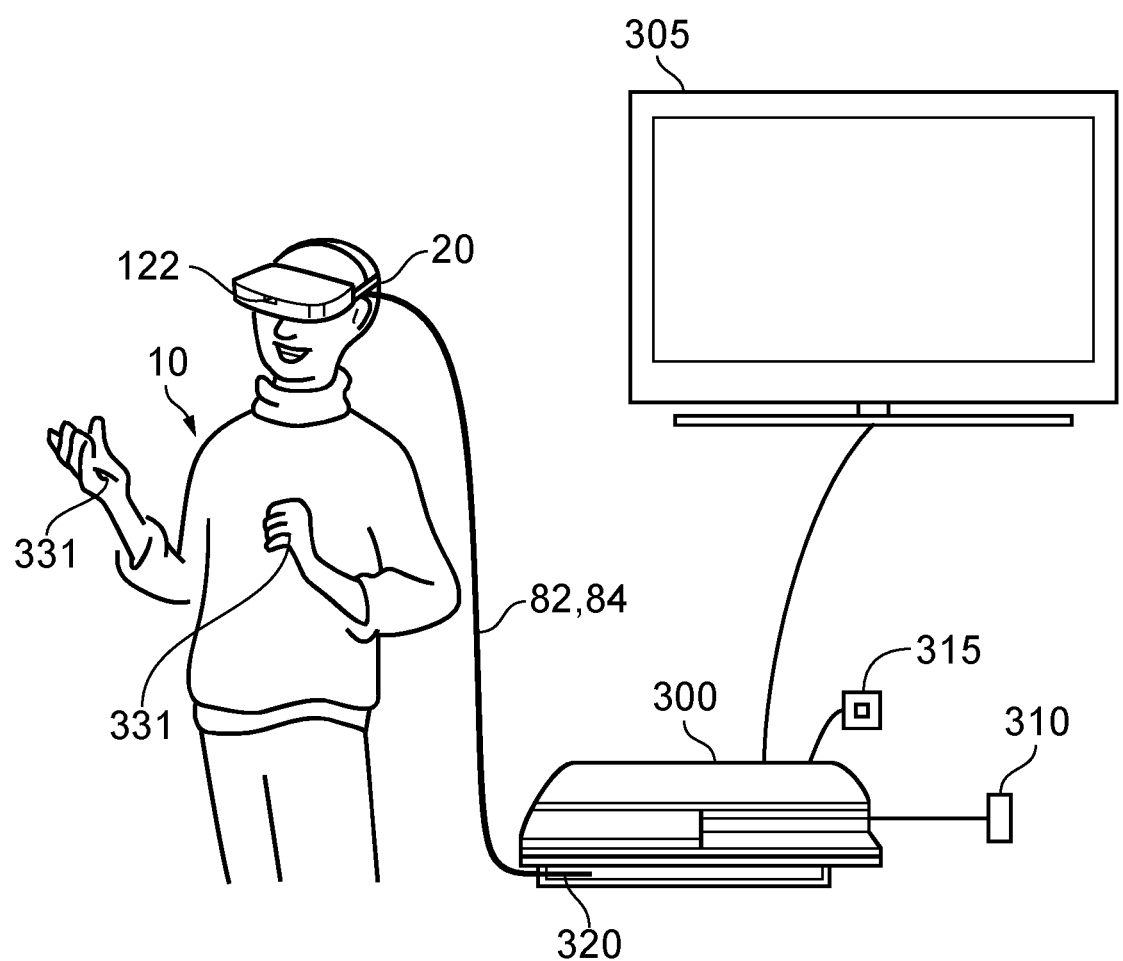
FIGS. 6 and 7 schematically illustrate a user wearing an HMD connected to a Sony® PlayStation 3® games console.

FIG. 6 schematically illustrates an example virtual reality system and in particular shows a user wearing an HMD connected to a Sony® PlayStation 3® games console 300 as an example of a base device. The games console 300 is connected to a mains power supply 310 and (optionally) to a main display screen (not shown). A cable, acting as the cables 82, 84 discussed above (and so acting as both power supply and signal cables), links the HMD 20 to the games console 300 and is, for example, plugged into a USB socket 320 on the console 300. Note that in the present embodiments, a single physical cable is provided which fulfils the functions of the cables 82, 84.

The video displays in the HMD 20 are arranged to display images generated by the games console 300, and the earpieces 60 in the HMD 20 are arranged to reproduce audio signals generated by the games console 300. Note that if a USB type cable is used, these signals will be in digital form when they reach the HMD 20, such that the HMD 20 comprises a digital to analogue converter (DAC) to convert at least the audio signals back into an analogue form for reproduction.

Images from the camera 122 mounted on the HMD 20 are passed back to the games console 300 via the cable 82, 84. Similarly, if motion or other sensors are provided at the HMD 20, signals from those sensors may be at least partially processed at the HMD 20 and/or may be at least partially processed at the games console 300. The use and processing of such signals will be described further below.

The USB connection from the games console 300 also provides power to the HMD 20, according to the USB standard.

FIG. 6 also shows a separate display 305 such as a television or other openly viewable display (by which it is meant that viewers other than the HMD wearer may see images displayed by the display 305) and a camera 315, which may be (for example) directed towards the user (such as the HMD wearer) during operation of the apparatus. An example of a suitable camera is the PlayStation Eye® camera, although more generally a generic "webcam", connected to the console 300 by a wired (such as a USB) or wireless (such as WiFi™ or Bluetooth®) connection.

The display 305 may be arranged (under the control of the games console) to provide the function of a so-called "social screen". It is noted that playing a computer game using an HMD can be very engaging for the wearer of the HMD but less so for other people in the vicinity (particularly if they are not themselves also wearing HMDs). To provide an improved experience for a group of users, where the number of HMDs in operation is fewer than the number of users, images can be displayed on a social screen. The images displayed on the social screen may be substantially similar to those displayed to the user wearing the HMD, so that viewers of the social screen see the virtual environment (or a subset, version or representation of it) as seen by the HMD wearer. In other examples, the social screen could display other material such as information relating to the HMD wearer's current progress through the ongoing computer game. For example, the HMD wearer could see the game environment from a first person viewpoint whereas the social screen could provide a third person view of activities and movement of the HMD wearer's avatar, or an overview of a larger portion of the virtual environment. In these examples, an image generator (for example, a part of the functionality of the games console) is configured to generate some of the virtual environment images for display by a display separate to the head mountable display.

In FIG. 6 the user is wearing one or two so-called haptic gloves 331. These can include actuators to provide haptic feedback to the user, for example under the control of processing carried out by the console 300. They may also provide configuration and/or location sensing.

Note that other haptic interfaces can be used, providing one or more actuators and/or one or more sensors. For example, a so-called haptics suit may be worn by the user. Haptic shoes may include one or more actuators and one or more sensors. Or the user could stand on or hold a haptic interface device. The one or more actuators associated with these devices may have different respective frequency responses and available amplitudes of vibration. Therefore in example arrangements to be discussed below the haptic generator can be responsive to attributes defining one or more capabilities of the haptic interface. In some examples, an attribute defines a frequency response of the haptic interface. In some examples, an attribute defines a maximum amplitude which may be represented by the haptic interface.

Figure 7:
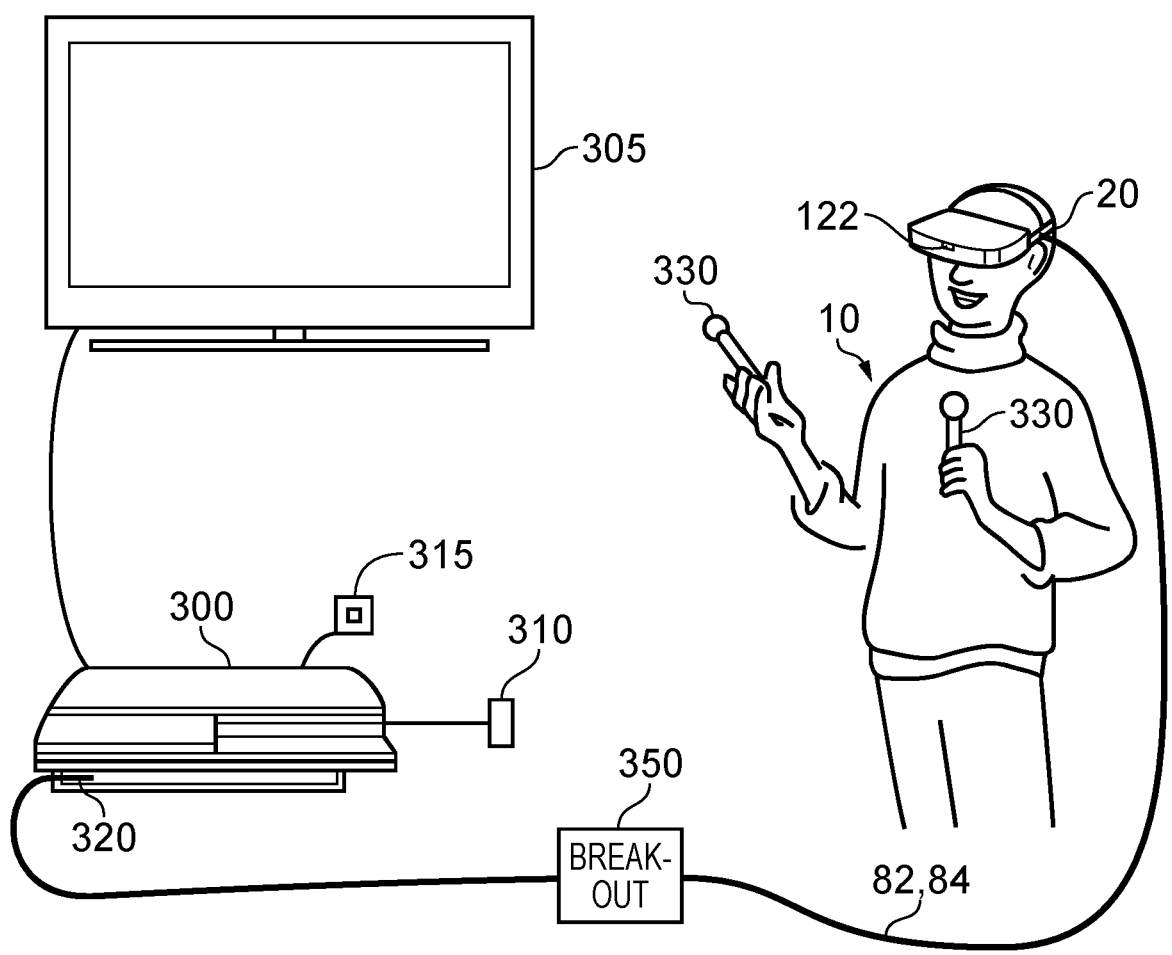

FIG. 7 schematically illustrates a similar arrangement (another example of a virtual reality system) in which the games console is connected (by a wired or wireless link) to a so-called "break out box" acting as a base or intermediate device 350, to which the HMD 20 is connected by a cabled link 82, 84. The breakout box has various functions in this regard. One function is to provide a location, near to the user, for some user controls relating to the operation of the HMD, such as (for example) one or more of a power control, a brightness control, an input source selector, a volume control and the like. Another function is to provide a local power supply for the HMD (if one is needed according to the embodiment being discussed). Another function is to provide a local cable anchoring point. In this last function, it is not envisaged that the break-out box 350 is fixed to the ground or to a piece of furniture, but rather than having a very long trailing cable from the games console 300, the break-out box provides a locally weighted point so that the cable 82, 84 linking the HMD 20 to the break-out box will tend to move around the position of the break-out box. This can improve user safety and comfort by avoiding the use of very long trailing cables.

In FIG. 7, the user is also shown holding a pair of hand-held controller 330s which may be, for example, Sony® Move® controllers which communicate wirelessly with the games console 300 to control (or to contribute to the control of) game operations relating to a currently executed game program. The user may also be wearing one or two haptic gloves as discussed in connection with FIG. 6.

It will be appreciated that the localisation of processing in the various techniques described in this application can be varied without changing the overall effect, given that an HMD may form part of a set or cohort of interconnected devices (that is to say, interconnected for the purposes of data or signal transfer, but not necessarily connected by a physical cable). So, processing which is described as taking place "at" one device, such as at the HMD, could be devolved to another device such as the games console (base device) or the break-out box. Processing tasks can be shared amongst devices. Source signals, on which the processing is to take place, could be distributed to another device, or the processing results from the processing of those source signals could be sent to another device, as required. So any references to processing taking place at a particular device should be understood in this context. Similarly, where an interaction between two devices is basically symmetrical, for example where a camera or sensor on one device detects a signal or feature of the other device, it will be understood that unless the context prohibits this, the two devices could be interchanged without any loss of functionality.

As mentioned above, in some uses of the HMD, such as those associated with virtual reality (VR) or augmented reality (AR) systems, the user's viewpoint needs to track movements with respect to a real or virtual space in which the user is located.

This tracking is carried out by detecting motion of the HMD and varying the apparent viewpoint of the displayed images so that the apparent viewpoint tracks the motion.

Figure 8:
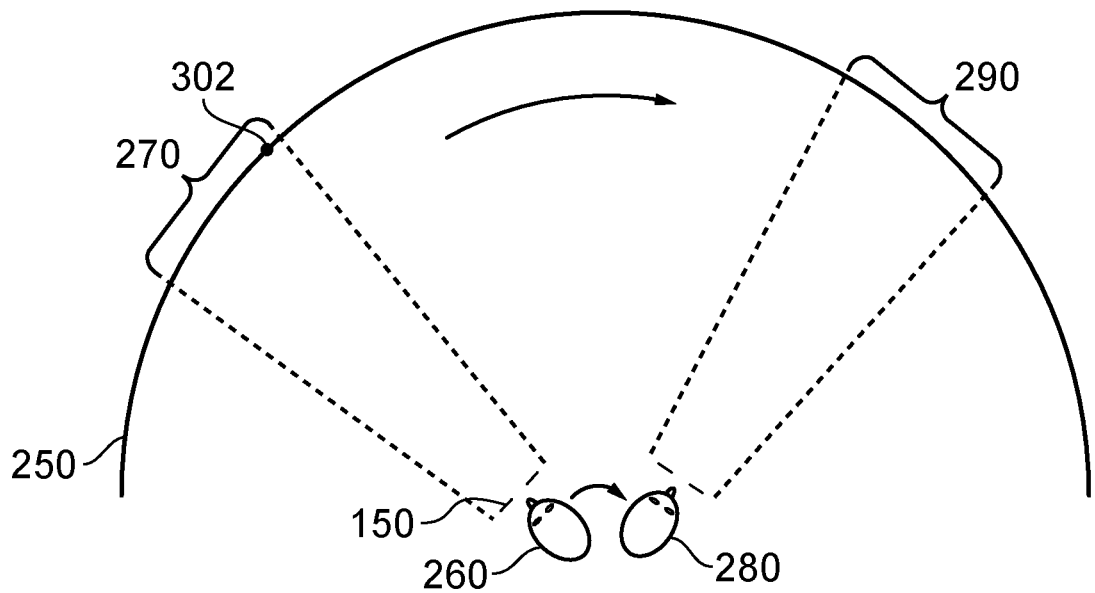
FIG. 8 schematically illustrates a change of view of user of an HMD.

FIG. 8 schematically illustrates the effect of a user head movement in a VR or AR system.

Referring to FIG. 8, a virtual environment is represented by a (virtual) spherical shell 250 around a user. This provides an example of a virtual display screen (VDS). Because of the need to represent this arrangement on a two-dimensional paper drawing, the shell is represented by a part of a circle, at a distance from the user equivalent to the separation of the displayed virtual image from the user. A user is initially at a first position 260 and is directed towards a portion 270 of the virtual environment. It is this portion 270 which is represented in the images displayed on the display elements 150 of the user's HMD. It can be seen from the drawing that the VDS subsists in three dimensional space (in a virtual sense) around the position in space of the HMD wearer, such that the HMD wearer sees a current portion of the VDS according to the HMD orientation.

Consider the situation in which the user then moves his head to a new position and/or orientation 280. In order to maintain the correct sense of the virtual reality or augmented reality display, the displayed portion of the virtual environment also moves so that, at the end of the movement, a new portion 290 is displayed by the HMD.

So, in this arrangement, the apparent viewpoint within the virtual environment moves with the head movement. If the head rotates to the right side, for example, as shown in FIG. 8, the apparent viewpoint also moves to the right from the user's point of view. If the situation is considered from the aspect of a displayed object, such as a displayed object 300, this will effectively move in the opposite direction to the head movement. So, if the head movement is to the right, the apparent viewpoint moves to the right but an object such as the displayed object 300 which is stationary in the virtual environment will move towards the left of the displayed image and eventually will disappear off the left-hand side of the displayed image, for the simple reason that the displayed portion of the virtual environment has moved to the right whereas the displayed object 300 has not moved in the virtual environment.

Figure 2:
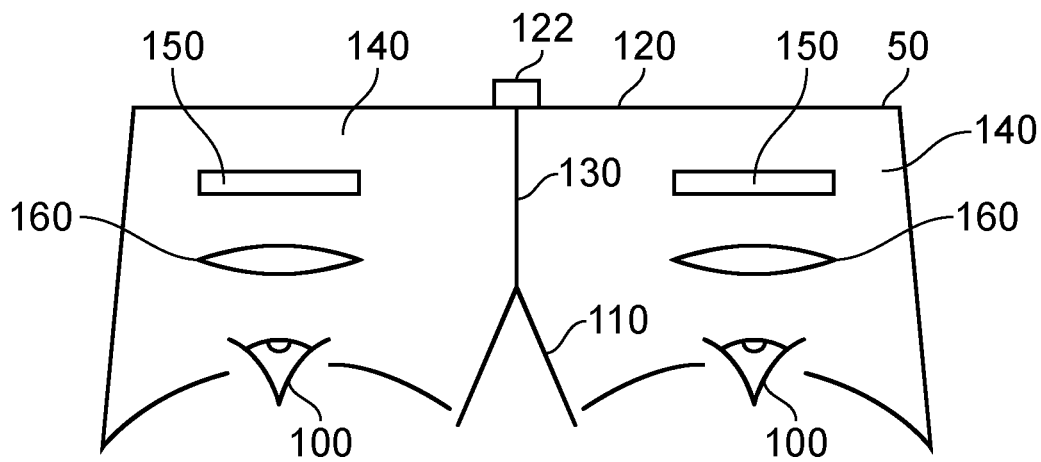
FIG. 2 is a schematic plan view of an HMD.
Figure 9A:
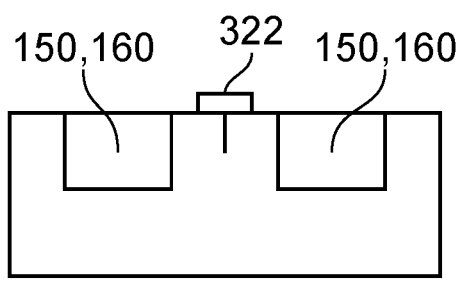
FIGS. 9a and 9b schematically illustrate HMDs with motion sensing.
Figure 9B:
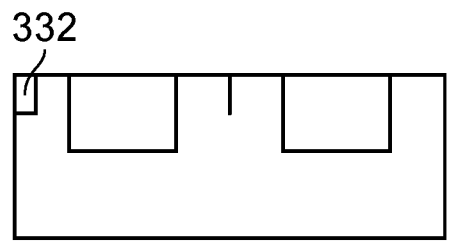

FIGS. 9a and 9b schematically illustrated HMDs with motion sensing. The two drawings are in a similar format to that shown in FIG. 2. That is to say, the drawings are schematic plan views of an HMD, in which the display element 150 and optical elements 160 are represented by a simple box shape. Many features of FIG. 2 are not shown, for clarity of the diagrams. Both drawings show examples of HMDs with a motion detector for detecting motion of the observer's head.

In FIG. 9a, a forward-facing camera 322 is provided on the front of the HMD. This may be the same camera as the camera 122 discussed above, or may be an additional camera. This does not necessarily provide images for display to the user (although it could do so in an augmented reality arrangement). Instead, its primary purpose in the present embodiments is to allow motion sensing. A technique for using images captured by the camera 322 for motion sensing will be described below in connection with FIG. 10. In these arrangements, the motion detector comprises a camera mounted so as to move with the frame; and an image comparator operable to compare successive images captured by the camera so as to detect inter-image motion.

FIG. 9b makes use of a hardware motion detector 332. This can be mounted anywhere within or on the HMD. Examples of suitable hardware motion detectors are piezoelectric accelerometers or optical fibre gyroscopes. It will of course be appreciated that both hardware motion detection and camera-based motion detection can be used in the same device, in which case one sensing arrangement could be used as a backup when the other one is unavailable, or one sensing arrangement (such as the camera) could provide data for changing the apparent viewpoint of the displayed images, whereas the other (such as an accelerometer) could provide data for image stabilisation.

Figure 10:
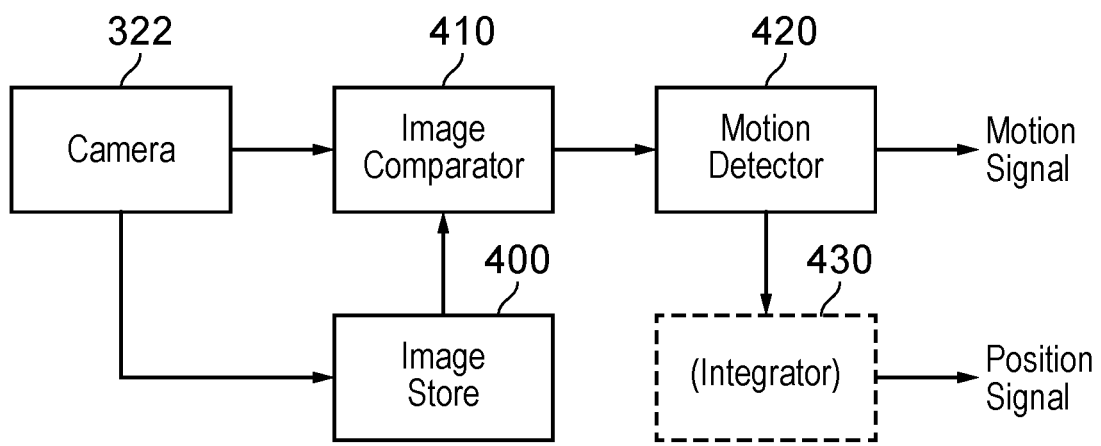
FIG. 10 schematically illustrates a position sensor based on optical flow detection.

FIG. 10 schematically illustrates one example of motion detection using the camera 322 of FIG. 9a.

The camera 322 is a video camera, capturing images at an image capture rate of, for example, 25 images per second. As each image is captured, it is passed to an image store 400 for storage and is also compared, by an image comparator 410, with a preceding image retrieved from the image store. The comparison uses known block matching techniques (so-called "optical flow" detection) to establish whether substantially the whole image has moved since the time at which the preceding image was captured. Localised motion might indicate moving objects within the field of view of the camera 322, but global motion of substantially the whole image would tend to indicate motion of the camera rather than of individual features in the captured scene, and in the present case because the camera is mounted on the HMD, motion of the camera corresponds to motion of the HMD and in turn to motion of the user's head.

The displacement between one image and the next, as detected by the image comparator 410, is converted to a signal indicative of motion by a motion detector 420. If required, the motion signal is converted by to a position signal by an integrator 430.

As mentioned above, as an alternative to, or in addition to, the detection of motion by detecting inter-image motion between images captured by a video camera associated with the HMD, the HMD can detect head motion using a mechanical or solid state detector 332 such as an accelerometer. This can in fact give a faster response in respect of the indication of motion, given that the response time of the video-based system is at best the reciprocal of the image capture rate. In some instances, therefore, the detector 332 can be better suited for use with higher frequency motion detection. However, in other instances, for example if a high image rate camera is used (such as a 200 Hz capture rate camera), a camera-based system may be more appropriate. In terms of FIG. 10, the detector 332 could take the place of the camera 322, the image store 400 and the comparator 410, so as to provide an input directly to the motion detector 420. Or the detector 332 could take the place of the motion detector 420 as well, directly providing an output signal indicative of physical motion.

Other position or motion detecting techniques are of course possible. For example, a mechanical arrangement by which the HMD is linked by a moveable pantograph arm to a fixed point (for example, on a data processing device or on a piece of furniture) may be used, with position and orientation sensors detecting changes in the deflection of the pantograph arm. In other embodiments, a system of one or more transmitters and receivers, mounted on the HMD and on a fixed point, can be used to allow detection of the position and orientation of the HMD by triangulation techniques. For example, the HMD could carry one or more directional transmitters, and an array of receivers associated with known or fixed points could detect the relative signals from the one or more transmitters. Or the transmitters could be fixed and the receivers could be on the HMD. Examples of transmitters and receivers include infra-red transducers, ultrasonic transducers and radio frequency transducers. The radio frequency transducers could have a dual purpose, in that they could also form part of a radio frequency data link to and/or from the HMD, such as a Bluetooth® link.

Figure 11:
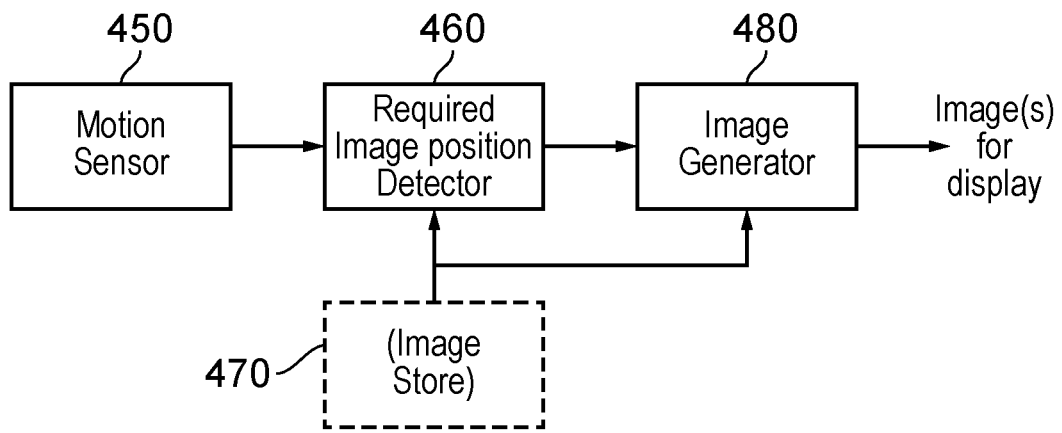
FIG. 11 schematically illustrates image processing carried out in response to a detected position or change in position of an HMD.

FIG. 11 schematically illustrates image processing carried out in response to a detected position or change in position of the HMD.

As mentioned above in connection with FIG. 10, in some applications such as virtual reality and augmented reality arrangements, the apparent viewpoint of the video being displayed to the user of the HMD is changed in response to a change in actual position or orientation of the user's head.

With reference to FIG. 11, this is achieved by a motion sensor 450 (such as the arrangement of FIG. 10 and/or the motion detector 332 of FIG. 9b) supplying data indicative of motion and/or current position to a required image position detector 460, which translates the actual position of the HMD into data defining the required image for display. An image generator 480 accesses image data stored in an image store 470 if required, and generates the required images from the appropriate viewpoint for display by the HMD. The external video signal source can provide the functionality of the image generator 480 and act as a controller to compensate for the lower frequency component of motion of the observer's head by changing the viewpoint of the displayed image so as to move the displayed image in the opposite direction to that of the detected motion so as to change the apparent viewpoint of the observer in the direction of the detected motion.

The operations to be discussed below relate to the adaptation of content output by an HMD in response to a well-being of the user 10 wearing the HMD 20 (for example being represented by a detected well-being metric or score to be discussed below). A wide range of users having different ages and varying physiological states may wear the HMD in order to view displayed content and listen to provided audio. For example, some users may be suffering from an illness (short-term or long-term) and may be feeling unwell, or some users may be intoxicated due to consumption of medication or alcohol. A minority of users may experience a modification of their physiological state when participating in a VR experience due to a sensory conflict between the visual and vestibular systems.

Figure 12:
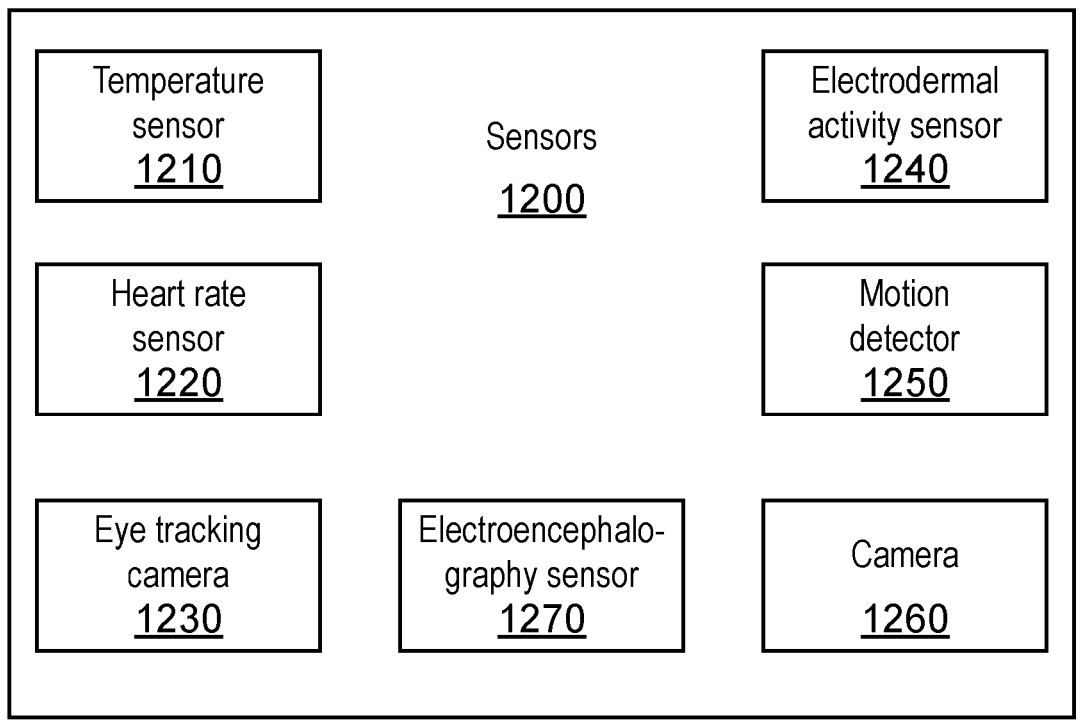
FIG. 12 schematically illustrates a functional block diagram of hardware to detect parameters indicating current properties of a user.

FIG. 12 illustrates a functional block diagram of hardware to detect parameters indicating a user's current properties. In embodiments of the disclosure, one or more sensors 1200 can be provided for detecting one or more parameters indicating one or more current properties (for example physiological properties, physiological properties associated with at least one of the user's eyes, or properties associated with user motion) of the user wearing the HMD, the one or more sensors comprising one or more from the list consisting of: a temperature sensor 1210; a heart rate sensor 1220; an eye tracking camera 1230; an electrodermal activity sensor 1240; a motion detector 1250; a camera 1260; and an electroencephalography sensor 1270.

For example, the temperature sensor 1210 may be an infrared thermometer configured to detect infrared radiation emitted from a portion of the user's body such as the user's ear 70 (eardrum) or the user's forehead. The infrared thermometer may comprise a lens to focus infrared radiation from the portion of the user's body onto an infrared radiation sensor and an electrical signal is generated by the sensor indicative of the temperature of the portion of the user's body. The temperature sensor 1210 can be configured to detect the infrared radiation emitted from the user's body either when in contact with the user's body or when not in direct contact with the user's body. The temperature sensor 1210 may be provided as part of the HMD and positioned on a portion of the HMD proximate (when being worn) to the user's forehead or either side of the user's forehead (temporal temperature measurement), or may be provided as part of the associated headphone audio transducers or earpieces 60 of the HMD which fit into the user's left and right ears 70 for tympanic temperature measurement. As such, the headphone audio transducers or earpieces (earbuds) 60 of the HMD may comprise one or more temperature sensors 1210 so that a temperature of the user's body can be identified from at least one of the user's ear canals. Alternatively or in addition, the temperature sensor 1210 may be positioned on another portion of the user's body such as the axilla, in which case the temperature sensor 1210 may be provided separate to the HMD and the temperature sensor may transmit data indicative of the one or more detected parameters via a wired or wireless communication such as one using the Bluetooth® protocol.

In embodiments of the disclosure, the HMD comprises one or more temperature sensors 1210 configured to detect one or more parameters indicating the temperature of the user's body. Alternatively or in addition, one or more sensors may be positioned on other respective portions of the user's body, and parameters indicative of the temperature of the user's body can be detected at the respective portions of the user's body. This provides an example of one or more temperature sensors 1210 configured to detect one or more parameters indicating a temperature of the body of the user wearing the HMD. More generally this provides an example of one or more sensors 1200 configured to detect one or more parameters indicating a physiological property of the user wearing the HMD.

In embodiments of the disclosure, one or more heart rate sensors 1220 may be provided either as part of the HMD or separate to the HMD. For example, the heart rate sensor 1220 may be positioned so as to contact the user's skin so that electrical activity associated with the contraction of the user's heart is detected by the heart rate sensor 1220 and one or more detected parameters provide an indication of the beating rate of the user's heart. Alternatively or in addition, the heart rate sensor 1220 may comprise an optical sensor and a plurality of light emitting diodes (LEDs) that emit light of different wavelengths in order to detect one or more parameters indicating the user's heart rate. The different wavelengths refract differently off the blood flowing through the user's body and the optical sensor detects one or more parameters associated with the refracted wavelengths indicative of the changes in the blood flow and the user's heart rate.

The HMD may comprise one or more heart rate sensors 1220 configured to detect one or more parameters indicating the beating rate of the user's heart and alternatively or in addition, one or more heart rate sensors 1220 may be provided separate to the HMD on respective portions of the user's body such as the arm, wrist or chest. In some examples, the HMD comprises one or more heart rate sensors 1220 positioned proximate to the user's neck, temporal artery (side of forehead), or ear canal. The heart rate sensor 1220 may be provided on a front portion of the HMD so that the heart rate sensor is proximate to or in contact with a side portion of the user's forehead proximate to the temporal artery. In some embodiments, two respective heart rate sensors may be positioned on either side of the forehead for respectively detecting parameters indicating the beating rate of the user's heart. Alternatively or in addition, one or more heart rate sensors 1220 may be provided as part of the associated headphone audio transducers or earpieces 60 of the HMD which fit into the user's left and right ears 70 so that one or more parameters indicating the beating rate of the user's heart can be detected from at least one of the user's ear canals.

Figure 13:
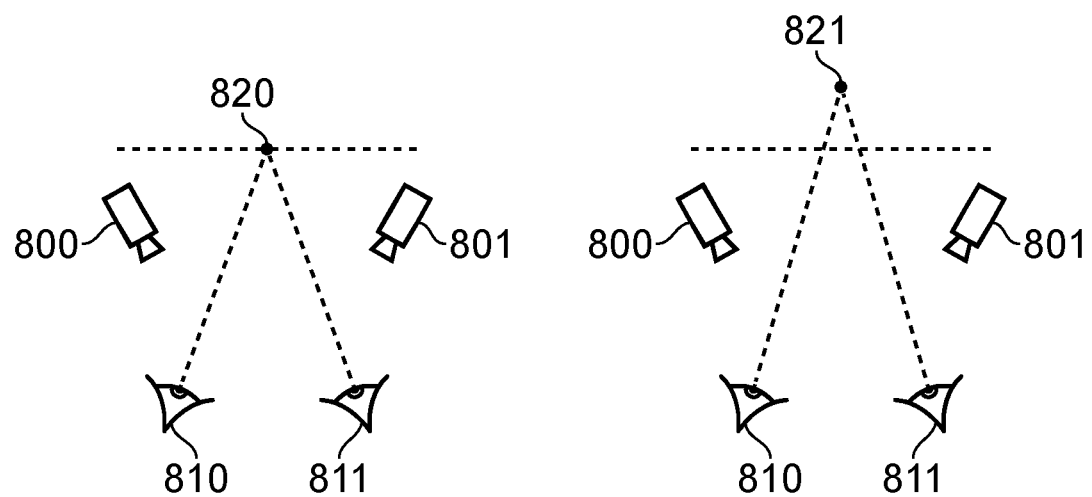
FIG. 13 schematically illustrates determining a point of focus using vergence of the eyes.

In embodiments of the disclosure, the HMD may comprise one or more eye tracking cameras 1230 configured to detect one or more parameters indicating a physical direction in which the eyes are pointing, or in other words, the direction of the user's gaze. For example, the HMD may comprise two respective eye tracking cameras 1230 used to detect the orientation of the user's eyes and one or more infrared or near-infrared light sources. The light source can be used to illuminate the user's eye to create reflections of the structure of the eye and the movement of each eye can be tracked by capturing successive images of the eye. FIG. 13 shows two eye tracking cameras 800 and 801 that are used to detect the orientation of the eyes 810 and 811 in a head mountable display device. By comparing information about the orientation of each eye 810/811, the so-called vergence of the eyes can be detected. The vergence can then be used to detect where on the display screen 820 (or with respect to a virtual image of a display, as in an HMD) the viewer is looking, and at which apparent depth the viewer is focussed on in the case of a 3D image. Alternatively, the orientation of just one of the eyes 810 and 811 can be used to determine a line of sight along which the user is focussed.

Referring again to FIG. 12, the HMD may comprise two respective eye tracking cameras 1230 to respectively track each eye and detect parameters indicating the direction of the user's gaze and/or the dilation of the user's pupils. The eye tracking cameras 1230 can be configured to capture successive images of the user's eyes and detect one or more parameters indicating the pattern of the user's gaze and/or the pattern of the dilation of the user's pupils. For example, the eye tracking cameras 1230 may detect parameters indicating the dilation of each of the user's pupils and the vergence of the user's eyes, which can be associated with a depth of focus of the eye. Variations in the pupil dilation, vergence of the eyes, and the depth of focus of the eyes can be identified from the detected parameters. For example, a sudden change in the pupil dilation may be indicative of a change in the user's current well-being, or a pattern of the pupil dilation or a pattern of the direction of the user's gaze such as a pattern of the vergence of the user's eyes, can also indicate an aspect of the user's current well-being.

In embodiments of the disclosure, one or more electrodermal activity sensors 1240 may be provided for detecting one or more parameters indicating the conductance of the user's skin also referred to as electrodermal activity or galvanic skin response. Sweat glands can secrete fluid through pores towards the skin surface and the secreted sweat influences the electrical characteristics of the skin surface such as conductance and resistance. The amount of sweat secreted by the user can be evaluated by providing one or more electrodermal activity sensors 1240 in contact with the user's skin, which detect one or more parameters indicating the electrical properties of the user's skin.

The HMD may comprise one or more electrodermal activity sensors 1240 configured to detect the one or more parameters indicating skin conductance, and alternatively or in addition, one or more electrodermal activity sensors 1240 may be provided separate to the HMD for respective portions of the user's body such as the hands, arms or axilla. For example, the HMD may comprise an electrodermal activity sensor 1240 that detects one or more parameters for identifying the electrical characteristics of a portion of the user's scalp. Alternatively or in addition, the earpieces 60 of the HMD which fit into the user's left and right ears 70 may comprise one or more electrodermal activity sensors 1240. One or more electrodermal activity sensors 1240 may be built-in to a handheld peripheral that is held by the user when wearing the HMD in order to detect parameters indicating the conductance of the skin on the user's hand.

In embodiments of the disclosure, one or more hardware motion detectors 1250, 332 (as illustrated in FIGS. 9A and 9B) can be mounted anywhere within or on the HMD and can detect one or more parameters indicating the motion and the average motion of the user's head. Examples of suitable hardware motion detectors are piezoelectric accelerometers or optical fibre gyroscopes. Alternatively or in addition, one or more motion detectors 1250, 332 can be provided separate to the HMD for respective portions of the user's body such as the user's arms, legs or chest, and the motion detectors 1250, 332 are configured to detect one or more parameters indicating the motion of the user's body and the average motion of the user's body.

Alternatively or in addition, camera-based motion detection can be implemented by providing the camera 1260, 322 mounted on at least one of the HMD or on the games console 300, and the technique of using images captured by the camera for motion sensing, as described previously with reference to FIG. 10, can be implemented. This means that one or more cameras can be mounted on the HMD or the games console 300 or both, and the one or more cameras are configured to detect one or more parameters indicating one or more current properties from the list consisting of: the motion of the user's head; the motion of the user's body; the average motion of the user's head; and the average motion of the user's body.

One or more parameters indicating the motion of the user's body or the motion of the user's head can be suitably detected by the one or more motion detectors 1250, 332 and the one or more cameras 1260, 322. An average of one or more of the detected parameters over a predetermined period of time can provide an indication of the average motion of the user's body or the average motion of the user's head for a predetermined time period. For example, a motion detector 1250 provided as part of the HMD can detect one or more parameters indicating the motion and/or current position of the user's head at a given time, and an average of the one or more parameters over a predetermined period of time can provide an indication of the average motion of the user's head for the period of time. One or more of the parameters detected by the motion detector 1250 may be averaged over a time period (such as 5, 10 or 30 minutes, for example) thus providing an indication of the average motion of the user's head, and the period of time over which one or more parameters are averaged may be suitably adjusted according to the user's preferences. Alternatively or in addition, one or more parameters that indicate the motion of the user's head may be detected by the one or more cameras 1260, 322 and the one or more parameters may be averaged over a predetermined period of time so as to provide an indication of the user's average head motion using camera based motion detection. It will be appreciated that an indication of the average motion of the user's head may be obtained by averaging one or more parameters detected by at least one of a motion detector 1250 provided as part of the HMD and one or more cameras 1260, 322 either provided as part of the HMD or separate to the HMD.

One or more motion detectors 1250, 332 can be provided separate to the HMD for respective portions of the user's body and one or more of the parameters detected by the one or more motion detectors can be averaged over a predetermined period of time. For example, one or more motion sensors may be provided on a user's leg (or both legs) and one or more parameters indicating the motion of the user's leg can be averaged over a predetermined period of time thus providing an indication of the average motion of the user's leg (or both legs) over the predetermined period of time. Similarly, one or more motion detectors may be provided for other portions of the user's body (e.g. each arm, the chest) and one or more detected parameters can be averaged for respective portions of the user's body such that an average motion of each arm may identified or an average motion of the user's chest may be identified. The average motion of the user's body may either represent an average motion for a portion of the user's body or may be obtained by combining the average motion for the respective portions of the user's body so that the average leg motion, the average arm motion and the average chest motion, for example, may be averaged to provide an indication of the average motion of the user's body. Alternatively or in addition, one or more cameras 1260, 322 may detect one or more parameters indicating motion of respective portions of the user's body and one or more of the parameters may be averaged over a given time period to provide an indication of the average motion of the portion of the user's body or to provide an indication of the average motion of the user's body. In embodiments of the disclosure, the HMD may comprise one or more electroencephalography sensors 1270 configured to detect one or more parameters indicating the electrical activity of the user's brain. For example, the electroencephalography sensor 1270 can comprise a plurality of electrodes that can be configured to detect voltage fluctuations resulting from current flow within the neurons of the brain. One or more of the electroencephalography sensors 1270 can be mounted on the HMD so that electrodes of the electroencephalography sensor 1270 can (when being worn) contact a portion of the user's scalp or forehead, and parameters indicative of electrical brain activity can be detected. In some examples, one or more electroencephalography sensors 1270 may be provided separate to the HMD and positioned on respective portions of the user's head. Alternatively or in addition, the earpieces 60 of the HMD which fit into the user's left and right ears 70 may comprise one or more electroencephalography sensors 1270. This means that one or more parameters indicating the electrical brain activity can be detected from either one of or both of the user's respective ear canals. This provides an example of one or more sensors 1200 configured to detect one or more parameters indicating a current property of the user wearing the HMD.

The one or more sensors 1200 provided as part of the HMD or separate to the HMD can communicate data indicative of the detected parameters to at least one of the HMD, the games console 300 or another device via a wired (physical cable) or a wireless communication link, and processing associated with the one or more parameters can be carried out at either the HMD or the games console 300 or both the HMD and games console 300 or another device. Alternatively or in addition, parameters from the one or more sensors may be at least partially processed at the HMD 20 and/or may be at least partially processed at the games console 300.

It will be appreciated that any of the sensors (1210, 1220, 1230, 1240, 1250, 1260, 1270) described can be configured to communicate data indicative of the one or more detected parameters to the HMD or the games console 300 or both via a wired or a wireless communication link, and parameters from the one or more sensors may be at least partially processed at the HMD 20 and/or may be at least partially processed at the games console 300.

Figure 14:
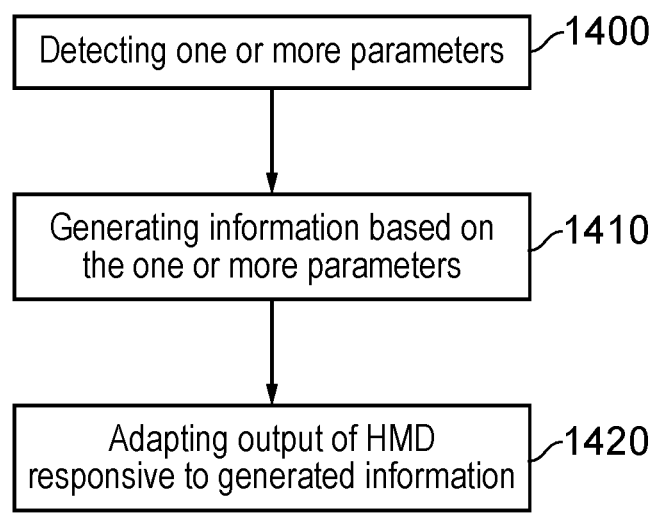
FIG. 14 is a schematic flowchart illustrating a method of adapting content.

Referring to FIG. 14, there is provided a schematic flowchart in respect of a method of adapting content (for example, for presentation by an HMD) responsive to a well-being of a user wearing an HMD comprising:

detecting (at a step 1400), by one or more sensors, one or more parameters indicating one or more current properties of the user wearing the HMD;

generating information (at a step 1410) indicating the well-being of the user based on the one or more parameters; and adapting an output of the HMD (at a step 1420) responsive to the generated information, the output comprising at least one of an image and an audio signal.

The adapted content can be presented to the user wearing the HMD, using the HMD as worn.

The one or more sensors 1200 may comprise any combination of the sensors 1210, 1220, 1230, 1240, 1250, 1260, 1270 which can be suitably mounted anywhere within or on the HMD or provided separate to the HMD. Each sensor can be configured to communicate data indicative of the one or more detected parameters to at least one of the HMD, the games console 300, the intermediate device 350 and another device comprising a CPU. It will be appreciated that the step 1410 of generating information indicating the well-being of the user (or at least indicating a detection of one or more metrics which can be indicative of well-being) can be performed by any of the HMD, the games console 300, the intermediate device 350, the one or more sensors or another device comprising a CPU, and processing tasks can be shared amongst respective devices. The generated information indicating the well-being of the user can be communicated either via a wired or wireless communication link between respective devices in order to share the generated information amongst the respective devices.

In some examples, the HMD may comprise one or more sensors in which case the HMD and its one or more sensors may be responsible for detecting (step 1400) the one or more parameters, generating the information (step 1410) indicating the well-being of the user and adapting (step 1420) the output of the HMD responsive to the generated information. Alternatively or in addition, some or all of the one or more sensors may communicate data indicative of the one or more detected parameters to the games console 300, the intermediate device 350 or another device comprising a CPU, and the step of generating information may be performed by the games console 300 or the intermediate device 350 or another device. Some or all of the one or more sensors may be provided separate to the HMD and the one or more sensors can be configured to communicate data indicative of the one or more detected parameters to at least one of the HMD, the games console 300, the intermediate device 350 or another device comprising a CPU, and the step 1410 of generating information can be performed by any device receiving the data indicative of the one or more parameters.

Data indicative of the generated information indicating the well-being of the user may be communicated to or from the HMD, the games console 300, the intermediate device 350 or any other respective device comprising a CPU. The step 1420 of adapting the output of the HMD responsive to the generated information can be performed by any of the HMD, the games console 300 or the intermediate device 350 according to whether the HMD, the games console 300 or the intermediate device 350 controls the content output by the HMD. For example, the image and the audio signal output by the HMD may be under the control of processing carried out by the games console 300, in which case the step of adapting the output of the HMD responsive to the generated information can be performed by the processor of the games console 300. Alternatively or in addition, the image and the audio signal output by the HMD may be at least partially (or entirely) under the control of processing carried out by the HMD, in which case the step of adapting the output of the HMD may be partially (or entirely) performed by the processor of the HMD.

Figure 15:
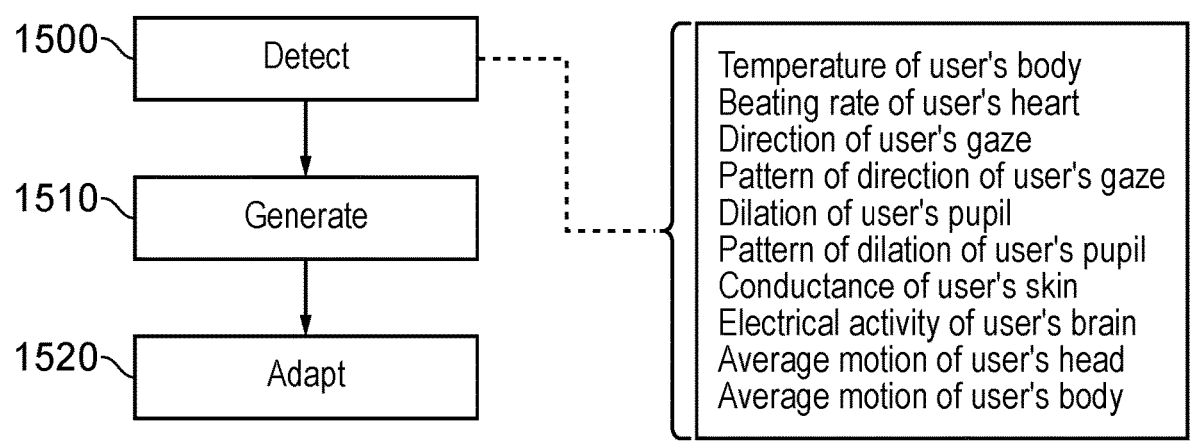
FIG. 15 is a schematic flowchart illustrating current properties of a user and a method of adapting content.

FIG. 15 is a schematic flowchart illustrating current properties of a user and a method of adapting content. At a step 1500 the one or more sensors detect one or more parameters indicating one or more current properties (e.g. physiological properties, properties associated with user motion) of the user comprising one or more from the list consisting of: a temperature of the user's body; a beating rate of the user's heart; a direction of the user's gaze; a pattern of the direction of the user's gaze; a dilation of at least one of the user's pupils; a pattern of the dilation of at least one of the user's pupils; a conductance of the user's skin; an electrical activity of the user's brain; an average motion of the user's head; and an average motion of the user's body. At a step 1510 the information indicating the well-being of the user is generated based on the one or more detected parameters indicating the one or more current properties of the user. At a step 1520 an output of the HMD comprising at least one of an image and an audio signal is adapted responsive to the generated information.

Figure 16:
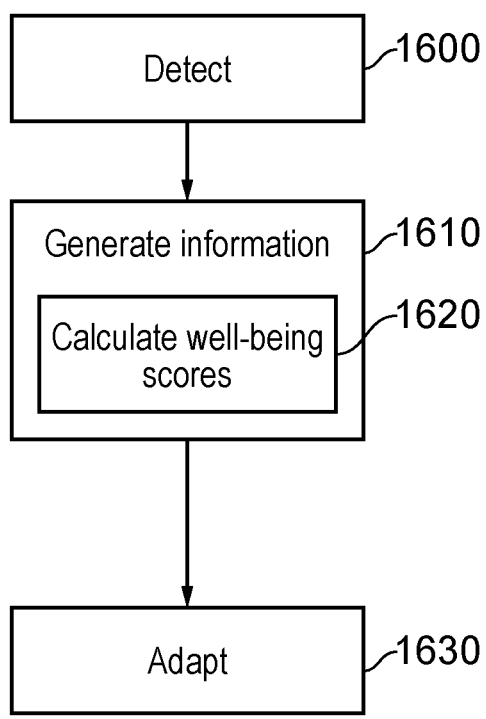
FIG. 16 is a schematic flowchart illustrating a method of adapting content using a well-being score.

FIG. 16 is a schematic flowchart illustrating a method of adapting content using a well-being score, comprising: detecting (at a step 1600), by one or more sensors, one or more parameters indicating one or more current properties of the user wearing the HMD;

generating information (at a step 1610) indicating the well-being of the user based on the one or more parameters and calculating, as part of the information, (at a step 1620) one or more respective well-being scores responsive to one or more of the detected parameters; and adapting (at a step 1630) the output of the HMD responsive to the generated information, the output comprising at least one of an image and an audio signal.

The step 1610 of generating the information and the step 1620 of calculating, as part of the information, the one or more respective well-being scores, can be performed by any of the HMD, the games console 300 or the intermediate device 350. The step 1620 of calculating, as part of the information, the one or more respective well-being scores can be performed by comparing one or more of the detected parameters with one or more reference parameters, and at least one of the image and the audio signal output by the HMD can be adapted based on the comparison. Note that in some cases not all of the one or more detected parameters are necessarily compared with a reference parameter, it may be the case that some of the detected parameters are not used for calculating a well-being score. For example, when two or more sensors of the same type are provided it may be possible to calculate a well-being score using parameters detected by just one sensor, or a single sensor may detect a plurality of parameters of which only some of the parameters are used for calculating a well-being score.

Alternatively or in addition, the one or more well-being scores can be calculated, as part of the information, by detecting a rate of change of one or more of the detected parameters and comparing the rate of change of one or more of the detected parameters with one or more rate of change reference parameters.

One or more reference parameters may be provided for each respective current property, and one or more of the detected parameters indicating a current property can be compared with one or more of the reference parameters for that current property in order to calculate a single well-being score for that current property. A first well-being score may be calculated for a first current property of the user and a second well-being score may be calculated for a second current property of the user, wherein the first well-being score represents a relationship between the first current property and a reference for the first current property and the second well-being score indicates a relationship between the second current property and a reference for the second current property.

For example, a well-being score may be calculated for the beating rate of the user's heart by comparing a reference parameter associated with the beating rate of the user's heart with a detected parameter indicating the beating rate of the user's heart. The well-being score for the beating rate of the user's heart may be represented as a value from 0 to 1 indicating the relationship between the beating rate of the user's heart and a reference beating rate of the user's heart. A reference beating rate of the user's heart may for example be set to 100 beats per minute, such that when the detected parameter indicates a beating rate of 100 beats per minute, the well-being score may have a value of 0.5. Alternatively, when the detected parameter indicates a beating rate of 150 beats per minute, the well-being score may have a value greater than or less than 0.5.

Alternatively or in addition, a well-being score associated with the average motion of the user's body may be calculated using one or more parameters detected by at least one of a motion sensor and a camera. One or more of the detected parameters can be averaged over a predetermined period of time and compared with a reference parameter associated with the average motion of the user's body. The reference parameter associated with the average motion of the user's body may be set depending on previously detected parameters or may be set depending on the type of content to be presented to the user wearing the HMD (e.g. type of game). It will be appreciated that a well-being score associated with the average motion of the user's head may be calculated in a similar manner.

The HMD may comprise a first heart rate sensor and in addition a second heart rate sensor may be provided separate to the HMD for a portion of the user's body such as the user's wrist. For this case, parameters detected by the first heart rate sensor may be considered in conjunction with parameters detected by the second heart rate sensor when calculating a well-being score associated with the user's heart rate. Alternatively, the well-being score associated with the user's heart rate may be calculated using parameters detected by either first heart rate sensor or the second heart rate sensor with more reliable measurements being given priority. For example, a first electrodermal activity sensor can be provided as part of the HMD and a second electrodermal activity sensor can be provided separate to the HMD and parameters detected by the two sensors can either be simultaneously considered when calculating a well-being score for the conductance of the user's skin or can be considered separately so that a well-being score is calculated using parameters detected by one of the sensors. Alternatively or in addition, a first well-being score may be calculated for a conductance of the user's skin using parameters detected by the first electrodermal activity sensor and a second well-being score may be calculated for a conductance of the user's skin using parameters detected by the second electrodermal activity sensor, such that two well-being scores may be calculated for the skin conductance for respective portions of the user's body.

Each reference parameter can have a value that is set according to an average behaviour expected for a typical user or may be calibrated for an individual user's current properties (for example physiological properties) based on previously detected parameters. The resting heart rate for a typical user can range from 60 to 100 beats per minute and may vary significantly from one user to the next, whereas the typical body temperature generally exhibits smaller variation from user to user. For example, a reference parameter associated with the temperature of the user's body may be set according to a typical temperature for a human body, which is expected to be approximately 37 degrees. As such, a well-being score may be calculated by comparing the reference parameter with the detected parameter so that a well-being score of approximately 0.5 is calculated when the detected parameter indicates that the user's body temperature is approximately 37 degrees. Alternatively or in addition, a reference parameter associated with the beating rate of the user's heart may be set according to an average heart rate for the user based on previously detected parameters indicating the user's heart rate. For example, previously recorded measurements may indicate that on average the user has a resting heart rate of approximately 80 beats per minute such that a reference parameter associated with this current property can be set based on the user's characteristics.

Alternatively or in addition, before viewing or listening to content output by the HMD or playing a game, the user may be presented with an introductory calibration stage so that one or more parameters indicating one or more current properties of the user can be detected prior to entering a game or viewing a movie output by the HMD. This means that reference values can be obtained for the one or more reference parameters, and the reference parameters can be calibrated for the individual user. Hence an alteration or a deterioration in the current properties of the user relative to the calibrated reference parameters can be detected and represented as one or more respective well-being scores.

Respective well-being scores can be calculated for respective current properties, and a respective well-being score is calculated responsive to one or more of the detected parameters indicating a corresponding current property. This means that changes in the one or more detected parameters indicating a current property will result in a change in the well-being score calculated for the current property, wherein the calculated well-being score may exhibit either a linear or a non-linear dependency upon changes in the one or more detected parameters.

It will be appreciated that well-being scores may be calculated on a basis other than comparison with a reference parameter. A rate of change of one or more of the detected parameters can be detected indicating a rate of change for one or more of the current properties of the user. For example, one or more parameters may be detected which indicate a sudden change in the user's heart rate or skin conductance over a period of time. A rate of change reference parameter associated with the beating rate of the user's heart may for example be set to ±15 beats per minute so that a detected change in the one or more parameters indicating the beating rate of the user's heart over a period of time can be compared with the rate of change reference parameter, and the value of the calculated well-being score is responsive to the rate of change of the one or more detected parameters with respect to the rate of change reference parameter.

The rate of change of the one or more parameters can be compared with a rate of change reference parameter for a current property, which represents a typically expected rate of change for the current property during normal conditions when playing a game or viewing a movie output by the HMD. As such, a well-being score can be calculated for a current property based on a comparison of the detected rate of change of the one or more parameters with the rate of change reference parameter. This means that the well-being score can be calculated according to a rate of change of the detected parameters and may be calculated irrespective of an absolute value associated with the one or more detected parameters. The rate of change reference parameter may be adjusted depending on the content output by the HMD, so that a first rate of change reference parameter is provided for a first current property for a first content and a second rate of change reference parameter is provided for the first current property for a second content.

Figure 17:
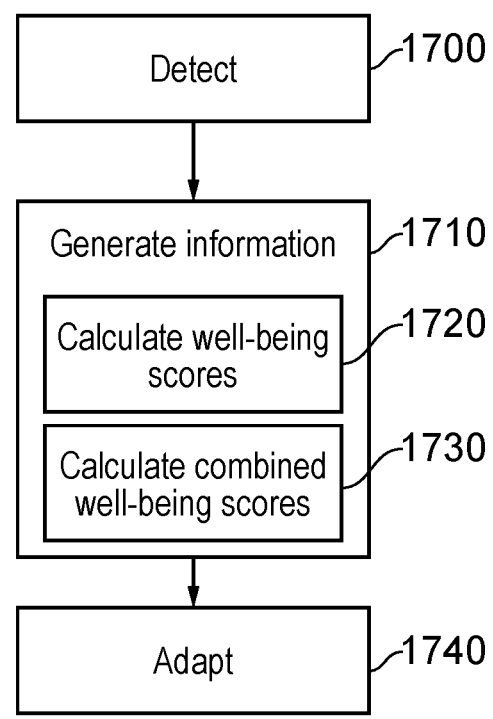
FIG. 17 is a schematic flowchart illustrating a method of adapting content using a combined well-being score.

Alternatively or in addition, a plurality of well-being scores may be calculated for which one or more of the well-being scores are calculated on the basis of a comparison of one or more detected parameters with one or more reference parameters, and one or more of the well-being scores are calculated on the basis of a comparison of the rate of change of one or more detected parameters with one or more rate of change reference parameters. FIG. 17 is a schematic flowchart illustrating a method of adapting content using a combined well-being score, comprising:

detecting (at a step 1700), by one or more sensors, one or more parameters indicating one or more physiological properties of the user wearing the HMD;

generating information (at a step 1710) indicating the well-being of the user based on the one or more parameters, and calculating, as part of the information, (at a step 1720) one or more respective well-being scores responsive to one or more of the detected parameters, and calculating, as part of the information, (at a step 1730) a combined well-being score by combining one or more respective well-being scores; and adapting (at a step 1740) the output of the HMD responsive to the generated information, the output comprising at least one of an image and an audio signal.

The steps 1710, 1720 and step 1730 of calculating, as part of the information, the combined well-being score by combining one or more respective well-being scores can be performed by any of the HMD, the games console 300 or the intermediate device 350 by either combining all of the respective well-being scores calculated at step 1720 or selectively combining the respective well-being scores for specific current properties, and at least one of the image and the audio signal output by the HMD can be adapted by comparing the combined well-being score with a threshold condition. As such, the calculated combined well-being score can represent the overall current condition (for example overall physiological condition) of the user, referred to as the well-being of the user. The step 1730 of calculating, as part of the information, the combined well-being score may be performed by combining all available respective well-being scores according to a weighted average where the weight assigned to each respective well-being score can be assigned a predetermined value or the user can adjust the weighting assigned for each well-being score. For example, each respective well-being score can be assigned an equal weighting or some well-being scores can be assigned a greater weighting so that some current properties (such as the beating rate of the user's heart or the pattern of the dilation of the user's pupils) can be considered high priority whilst other current properties can be considered low priority. As such, a priority level may be assigned for each respective well-being score, the priority level determining the weighting factor for a well-being score.

Figure 18A:
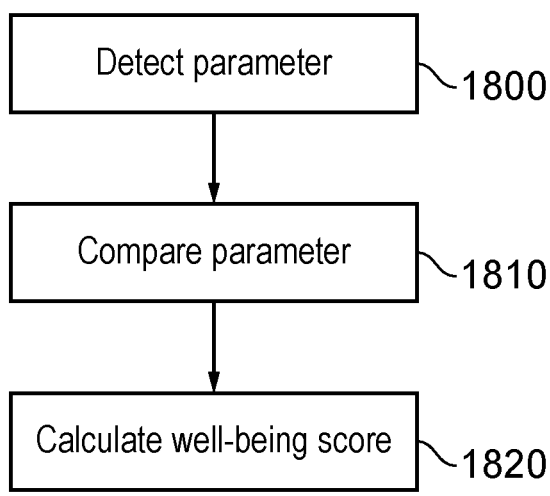
FIG. 18a is a schematic flowchart illustrating a method of calculating a well-being score using a reference parameter.
Figure 18B:
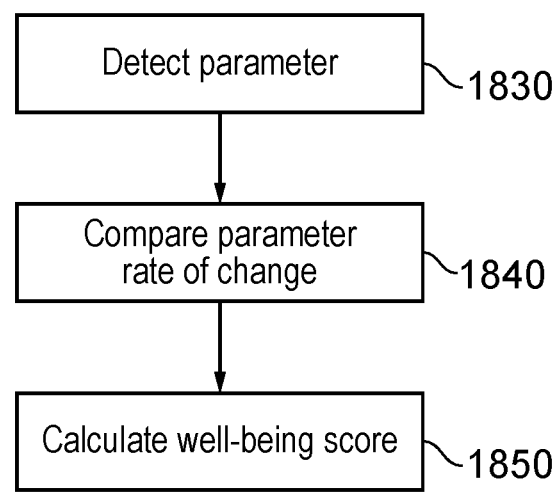
FIG. 18b is a schematic flowchart illustrating a method of calculating a well-being score using a rate of change reference parameter.

In some examples, one or more current properties may be more reliably measured than others, or some current properties may be more closely related than others, whilst some current properties may be considered higher priority with respect to the user's overall well-being. As such, the step 1730 of calculating the combined well-being score may be calculated by combining the well-being scores according to a priority level associated with each respective well-being score. The combined well-being score may be calculated by combining the well-being scores corresponding to the highest priority current properties and not combining the well-being scores corresponding to the lowest priority current properties. Alternatively or in addition, current properties that are more closely related to each other may be combined FIG. 18a is a schematic flowchart illustrating a method of calculating a well-being score using a reference parameter, comprising: detecting (at a step 1800), by one or more sensors, one or more parameters indicating one or more current properties of the user wearing the HMD;

comparing (at a step 1810) one or more of the detected parameters with one or more reference parameters; and calculating (at a step 1820) one or more respective well-being scores;

FIG. 18b is a schematic flowchart illustrating a method of calculating a well-being score using a rate of change reference parameter, comprising:

detecting (at a step 1830), by one or more sensors, one or more parameters indicating one or more current properties of the user wearing the HMD;

comparing (at a step 1840) a rate of change of one or more of the detected parameters with one or more rate of change reference parameters; and calculating (at a step 1850) one or more respective well-being scores.

One or more of the respective well-being scores can be combined and a combined well-being score can be compared with a threshold condition. Based on the comparison of the combined well-being score with the threshold condition, at least one of the image and the audio signal output by the HMD can be adapted. The threshold condition may comprise a plurality of respective threshold levels and the output of the HMD can be adapted responsive to whether the combined well-being score is less than or greater than a threshold level. For example, for a combined well-being score having a range of possible values between 0 and 1, the respective threshold levels of the threshold condition may be set to 0.2, 0.4, 0.6 and 0.8 (other values may similarly be considered). For a calculated well-being score of 0.5 this can mean that the audio signal and/or the image can be output by the HMD in their un-adapted state. Changes in the one or more parameters detected for the one or more current properties of the user may cause the value of the combined well-being score to change so that the value of the combined well-being score may exceed a first threshold level (e.g. 0.6), or may exceed a second threshold level (e.g. 0.8), or may be less than a third threshold level (e.g. 0.4), for example. The output of the HMD can be adapted by comparing the combined well-being score with each respective threshold level of the threshold condition. A threshold condition can comprise a plurality of respective threshold levels, the combined well-being score can be compared with each respective threshold level and the output of the HMD can be adapted responsive to whether the combined well-being score is greater than or less than a respective threshold level. This means that the output of the HMD can be adapted responsive to the generated information and the output may be adapted with varying degrees depending on the number of respective threshold levels of the threshold condition.

Figure 19A:
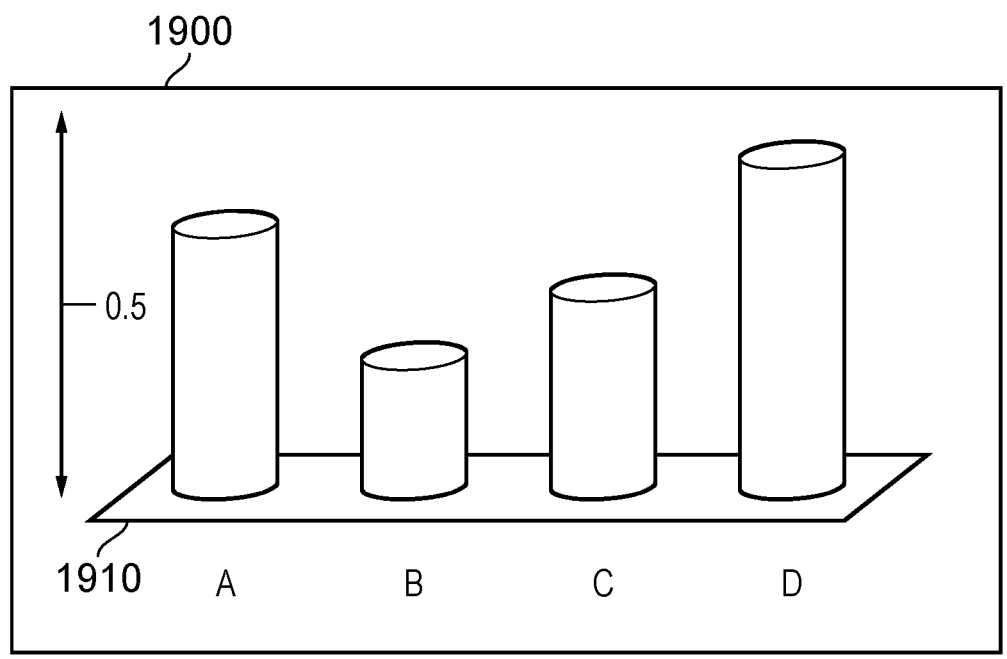
FIG. 19a schematically illustrates an image comprising a visual metric indicating one or more respective well-being scores.

FIG. 19a schematically illustrates an image comprising a visual metric indicating one or more respective well-being scores. In this example, the image 1900 comprises the visual metric 1910 which indicates four respective well-being scores for four respective current properties A, B, C, D. The well-being score labelled A is calculated responsive to the one or more parameters detected for a first current property, well-being score labelled B is calculated responsive to the one or more parameters detected for a second current property, well-being score labelled C is calculated responsive to the one or more parameters detected for a third current property, and well-being score labelled D is calculated responsive to the one or more parameters detected for a fourth current property. For example, the letter A may be suitably replaced with the words "body temperature" when the well-being score labelled A is calculated responsive to one or more parameters indicating the temperature of the user's body. Similarly, the letter B may be suitably replaced with the words "heart rate", the letter C may be suitably replaced with the words "skin conductance" and the letter D may be suitably replaced with the words "Brain electrical activity" (other current properties listed in FIG. 15 are also considered) so that each respective well-being score can be identifiably associated with a corresponding current property. Each well-being score indicated by the visual metric can be identifiably associated with a corresponding current property and displayed in a respective portion of the image output by the HMD. This provides an example of adapting an image 1900 output by the HMD by providing a visual metric 1910 indicating one or more respective well-being scores calculated responsive to one or more parameters detected for the user wearing the HMD.

The visual metric can be customized for each individual user so that well-being scores can be indicated according to the priority level assigned to each well-being score. For example, respective well-being scores may be indicated with an ordering determined by the priority level assigned to each well-being score, so that the highest priority well-being scores have precedence over the lowest priority well-being scores and some of the lowest priority well-being scores may not be provided in the visual metric 1910.

For example, the HMD may comprise a first electrodermal activity sensor 1240, and a second electrodermal activity sensor 1240 may be provided separate to the HMD for a respective portion of the user's body (such as the user's hands). A first well-being score can be calculated for the one or more parameters detected by the first electrodermal activity sensor and a second well-being score can be calculated for the one or more parameters detected by the second electrodermal activity sensor, such that the letter A can be replaced with the words "skin conductance for a first portion of the user's body" and the letter B can be replaced with the words "skin conductance for a second portion of the user's body" and the two well-being scores are respectively indicated for the same current property detected for different portions of the user's body. Alternatively, the one or more parameters detected by the two respective electrodermal activity sensors may be combined together to calculate a single well-being score that is indicated by the visual metric, such that the letter A can be replaced with the words "skin conductance".

It will be appreciated that the visual metric 1910 can be provided as illustrated in FIG. 19a, or the visual metric can be provided in a first portion of the image so that a second portion of the image, which is larger than the first portion, displays content such as a game or movie that can be adapted responsive to the calculated well-being scores. This means that the user can view the image 1900 output by the HMD and simultaneously view content (e.g. a game or a film) in the second portion of the image while being informed of the one or more respective well-being scores, wherein the second portion of the image can be adapted in accordance with one or more of the well-being scores respectively indicated by the visual metric 1910 in the first portion of the image.

Figure 19B:
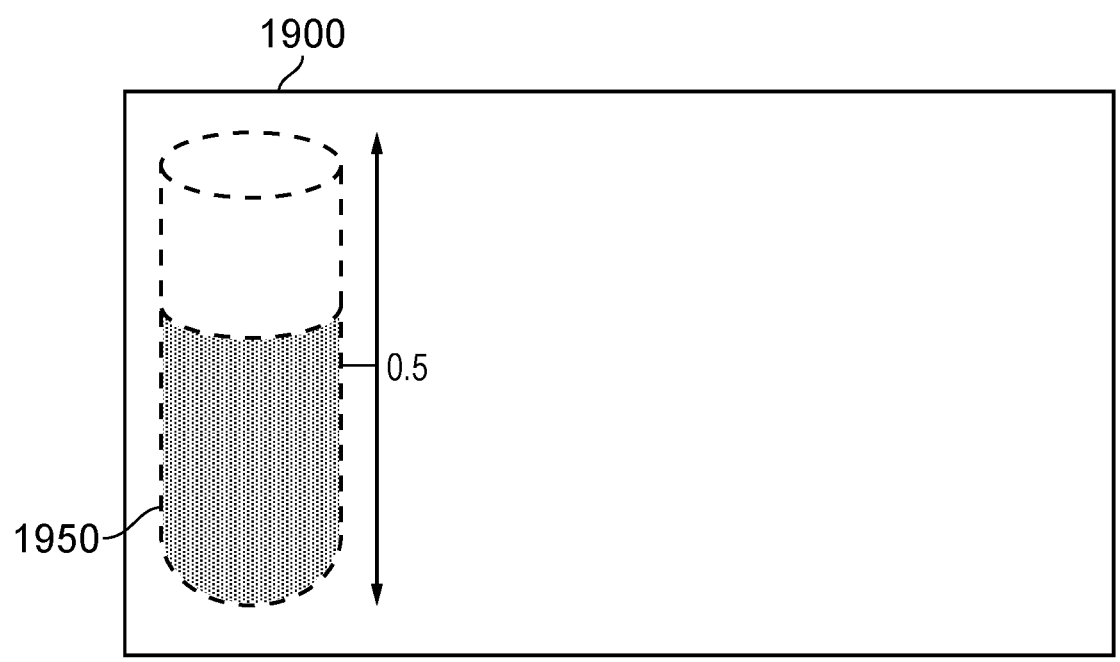
FIG. 19b schematically illustrates an image comprising a visual metric indicating a combined well-being score.

FIG. 19b schematically illustrates a visual metric indicating a combined well-being score. The visual metric 1950 can be configured to indicate a single combined well-being score, which is calculated by combining one or more of the respective well-being scores. Note that in some cases the visual metric may indicate a combined well-being score calculated by either combining all of the calculated respective well-being scores or selectively combining some of the respective well-being scores. Each user can customize the visual metric 1950 so that the combined well-being score indicated by the visual metric 1950 is calculated by selecting specific well-being scores according to the user's preference. For example, the user may assign a priority level to each well-being score, such that some well-being scores are not included in the step of calculating the combined well-being score. This means that the user can customize the visual metric 1950 so that a combined well-being score is indicated based on one or more current properties selected by the user.

It will be appreciated that the visual metric 1950 can be provided as illustrated in FIG. 19*b* so that the visual metric 1950 is provided in a first portion of the image and content such as a game or movie is displayed in a second portion of the image so that the user may monitor the current status of the combined well-being score when simultaneously viewing a game or movie or other content in the second portion of the image. This means that the properties of the second portion of the image can be adapted in accordance with the combined well-being score indicated in the first portion of the image.

The techniques to be discussed below are applicable to three-dimensional images output by the HMD. The depth of an image feature in a three-dimensional image is represented by its so-called disparity between the pair of stereoscopic images. In some examples, an image feature representing an object at infinity would generally have zero disparity, with disparity increasing as the object is closer to the viewpoint of the image.

Figure 20:
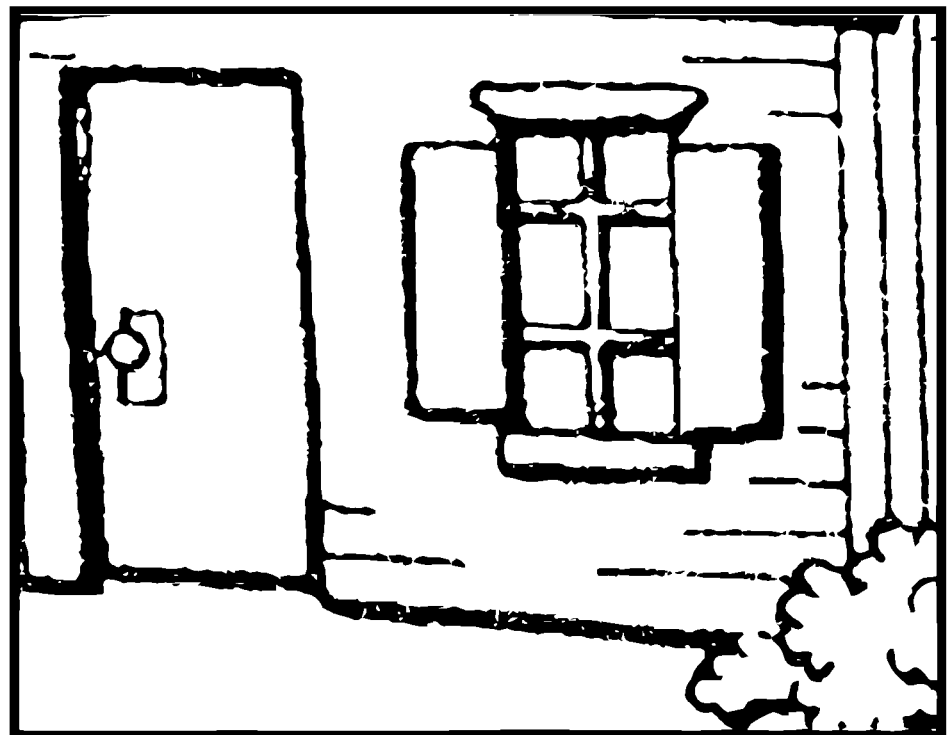
FIG. 20 schematically illustrates an image that is adapted to adjust the field of view.
Figure 20:
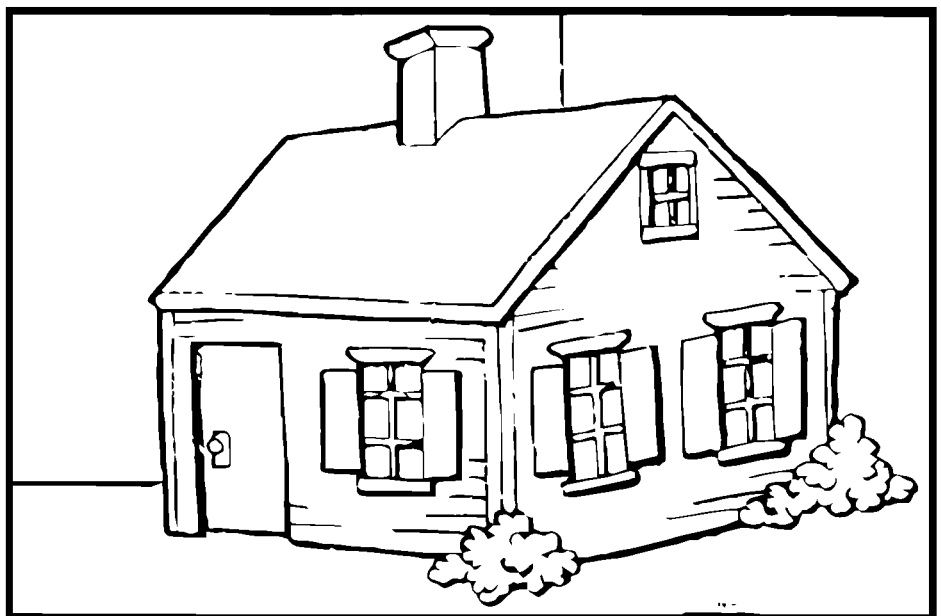

FIG. 20 schematically illustrates an image that is adapted to adjust the field of view. For an image of a virtual environment, the field of view of the image, or field of vision, represents the extent of the virtual environment that is observable at a given time and the field of view can be specified in degrees or radians. In embodiments of the disclosure the step of adapting the output of the HMD responsive to the generated information comprises adjusting a field of view for an image output by the HMD. When displaying the image of the virtual environment to the user wearing the HMD, the field of view of the image can be adjusted responsive to the generated information indicating the well-being of the user by controlling the image generator (for example, a part of the functionality of the games console or the HMD or both) responsible for generating the image output by the HMD.

An image of a virtual environment is shown for a first field of view 2010 and a second field of view 2020, in which a larger portion of the virtual environment is displayed for the second field of view 2020 than the first field of view 2010. The image can be generated at a time t1 with the first field of view 2010, and the field of view for the image can be adjusted responsive to the generated information indicating the well-being of the user so that the image of the virtual environment may be generated with the second field of view 2020 at a time t2, where the time t2 is later than the time t1, or vice versa.

For example, the HMD wearer may observe the virtual environment from a first person viewpoint, a third person viewpoint, or a viewpoint giving an overview of the virtual environment, where each viewpoint has a different field of view (the overview viewpoint displays the largest portion of the virtual environment at a given time). The field of view for the image can be adjusted by changing the position of the viewpoint to correspond to either the first person viewpoint or the third person viewpoint or the overview viewpoint or any intermediate position between these viewpoints responsive to the generated information.

For some applications (such as some first person shooter games) it may be undesirable to switch from the first person viewpoint to an overview viewpoint. For the first person viewpoint, an image displayed with a small field of view (such as 30 degrees) may mean that the user experiences a feeling of tunnel vision with minimal peripheral vision provided, which may give rise to a disconnect between the user's natural field of view and the field of view of the image output by the HMD. The average person has a field of view of approximately 135 degrees vertical and 200 degrees horizontal when combining the fields of view for the two eyes, and the binocular field of view where the two monocular fields of view overlap is approximately 120 degrees horizontally. The image generator can be controlled responsive to the information generated based on the one or more detected parameters so that the angular extent of the field of view for the image with the first person viewpoint can be adjusted to have a horizontal field of view ranging from 210 degrees to 60 degrees. In some examples, the horizontal field of view for the image output by the HMD can be adjusted to 210 degrees, 180 degrees, 150 degrees, 120 degrees, 90 degrees or 60 degrees responsive to the information generated based on the one or more detected parameters. Each respective field of view may have an associated threshold with which the generated information can be compared so that an angular extent of the field of view can be adapted responsive to a comparison of the generated information with a threshold associated with each respective field of view.

Figure 21:
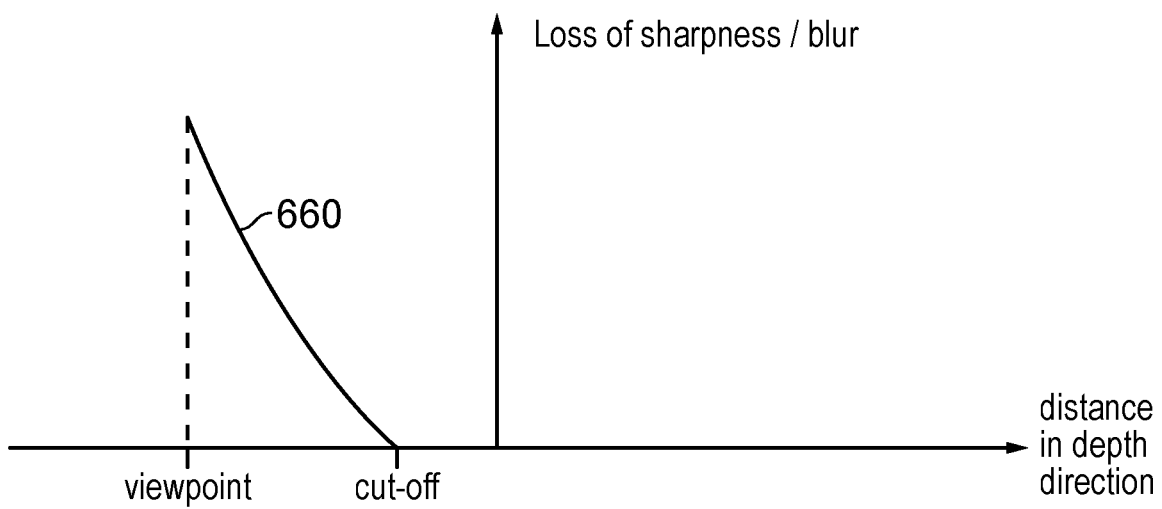
FIG. 21 schematically illustrates a blurring function varying with respect to distance in a depth direction from a viewpoint of an image.

FIG. 21 schematically illustrates a blurring function varying with respect to distance in a depth direction from a viewpoint of an image. The graph shows increasing blurriness (equivalent to the loss of sharpness) on the vertical axis with depth separation from the viewpoint on the horizontal axis. Depth of field is defined as the size of the region (in the depth direction) in which an image is sufficiently well focussed for an application. In embodiments of the present disclosure the step of adapting the output of the HMD responsive to the generated information comprises adjusting a depth of field in the image output by the HMD. A blurring function 660 may be applied for the image so that a foreground portion of the image is blurred, whilst no blurring or a smaller degree of blurring is applied for a background portion of the image. The blurring function 660 can be applied so that the magnitude of the degree of blurring varies according to a distance in the depth direction from the viewpoint of the image. This means that objects or other features that are displayed near to the viewpoint of the image in the depth direction can be rendered with a greater apparent blurriness than objects or other features displayed further from the viewpoint in the depth direction. As such, the objects or other features in the foreground of the image can be deemphasized with respect to the objects of other features in the background of the image, and the user's focus is more likely to be drawn away from the foreground portion of the image. This means that the user's focus may be more likely to be drawn towards a position in the background portion of the image (such as the horizon). The movement of the more sharply focussed objects and other features present in the background portion of the image may generally be easier for the user to mentally anticipate as they appear to move with a lower velocity relative to the viewpoint in comparison with objects and other features present in the foreground. Rapid changes in the vergence angle of the user's eyes may be deterred thus minimising visual discomfort and eye fatigue.

It will be appreciated that the gradient of the blurring function 660 shown in FIG. 21 can be adjusted and the cut-off point may be positioned at any distance in the depth direction with respect to the viewpoint depending on the properties of the scene displayed in the image. The gradient of the blurring function 660 and the position of the cut-off point can be adjusted responsive to the generated information indicating the well-being of the user. For example, the cut-off point may be set to be proximate to the viewpoint and depending on the information indicating the well-being of the user, the position of the cut-off point may be adjusted to a position further away from the viewpoint in the depth direction so that the blurring function 660 is applied for a larger portion of the foreground of the image. The position of the cut-off point can be adjusted responsive to the information indicating the user's well-being so that the blurring function 660 is applied for a larger or smaller portion of the image according to the user's well-being.

The blurring function describes the 'amount' of blurring to apply, and this blurring can be applied using any appropriate method, an example of which is now described.

Gaussian blur is a common method used to apply blur to images by using a Gaussian function to produce a weighting function in order to generate new values for pixels based upon the value of the pixels about them. This reassigning of pixel values based upon the values of surrounding pixels generates a blurrier image by reducing the variation between neighbouring pixels. A general two-dimensional Gaussian function is:

$$G(x, y) = \frac{1}{2\pi\sigma^2} e^{-\frac{x^2+y^2}{2\sigma^2}}$$

where σ is the standard deviation of the Gaussian function (representing the amount or degree of blur to be applied in the present example). This function generates sets of concentric circles of equal value about a point, the values of which are used as weightings when assigning a new value to pixels. The distribution that is generated is used to build a kernel (also known as a convolution matrix) which is applied to the original image, the result of which is a weighted averaging of a pixel's value depending on neighbouring pixels.

The kernel that is generated describes a convolution such that a pixel's original value has the highest weighting and the weighting of nearby pixel values decreases with distance from the pixel the blurring is being applied to. The weighting (and thus the degree of blurriness that is applied) may be varied by changing the value of σ, as a small value of σ produces a narrower, taller Gaussian distribution which results in the pixel to which the blurring is applied remaining largely unchanged because the weighting of surrounding pixels is much lower in comparison; this corresponds to a small degree of blurring. Varying σ in the opposite direction, a larger value of σ will result in a broader distribution in which the pixel value weighting decreases more slowly with distance from the original pixel; this translates to a greater degree of blurring than the smaller value of σ. Relating this to a generated blurring function, it is apparent that a Gaussian blur could be applied to image elements at each depth with a varying σ value.

Alternatively or in addition, the foreground region of the image and the objects and other features in the foreground region of the image may be deemphasized by adjusting the brightness of the foreground portion of the image relative to the brightness of the background portion of the image. The background portion of the image may be displayed with a greater brightness than the foreground portion of the image, which may encourage the user to direct their focus towards the background portion of the image.

In embodiments of the disclosure the output of the HMD can be adapted responsive to the generated information indicating the well-being of the user by adjusting either the number of virtual objects represented in the image or the texture resolution of each respective virtual object in the image based one or more from the list consisting of: a depth position of each virtual object in the image with respect to the viewpoint of the image; a geometric size of each virtual object in the image; a priority value associated with each virtual object in the image; and a position of each virtual object in the image with respect to either an avatar representation of the user or a viewpoint of the image.

Figure 22:
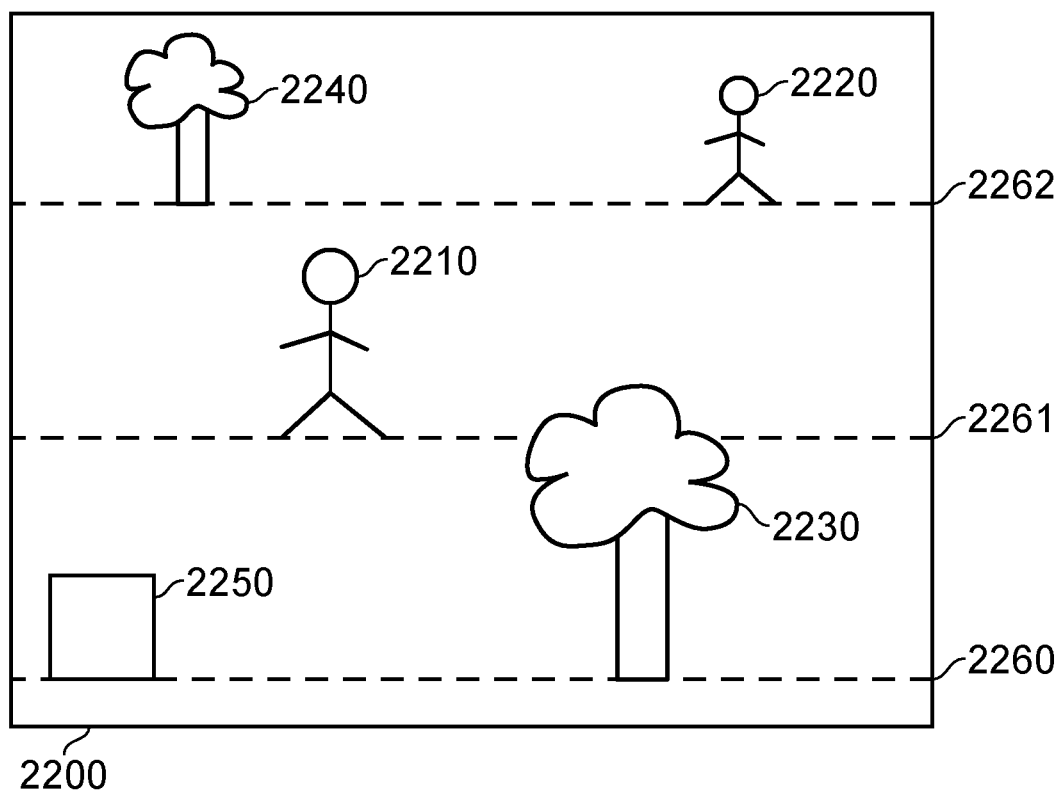
FIG. 22 schematically illustrates an image that is adapted to adjust the number of virtual objects in the image.

FIG. 22 schematically illustrates an image that is adapted to adjust the number of virtual objects in the image. Five respective virtual objects 2210, 2220, 2230, 2240 and 2250 are shown in the image 2200 for three different positions 2260, 2261, 2262 in the depth direction from the viewpoint of the image, where 2260 represents a depth position that is closer to the viewpoint of the image than the depth position 2261, and 2262 represents a depth position furthest away from the viewpoint of the image. Note that the geometric size of the first avatar 2210 is larger than that of the second avatar 2220, and the first tree 2230 is larger than the second tree 2240, because the first avatar and the first tree are positioned closer to the viewpoint in the depth direction. The method step of adapting the image output by the HMD may comprise adjusting the number of the respective virtual objects 2210, 2220, 2230, 2240 and 2250 in the image 2200. For example, the image 2200 may be adapted to remove one or more virtual objects based on their depth position with respect to the viewpoint of the image so that an object positioned at a depth position near to the viewing point may be removed. Similarly, the image 2200 can be adapted to adjust the number of virtual objects in the image based on a position of each virtual object in the image with respect to either an avatar representation of the user in the image 2200 or a viewpoint of the image 2200. Objects with a depth position near to the viewing point have a large disparity between the pair of stereoscopic images viewed by the user. Viewing these objects may require the user to converge their eyes while maintaining a focal length corresponding to the position of the display, which can result in the user crossing their eyes resulting in visual discomfort. As such, the image may be adapted responsive to the generated information to adjust the number of objects to reduce possible visual discomfort experienced by the user. For example, the image 2200 may be adapted responsive to the generated information to adjust the number of virtual objects in the image by removing either the first tree 2230 or the box 2250 at the depth position 2260, and these objects may be either removed or added back in to the image responsive to the generated information. It will be appreciated that the number of virtual objects can be adjusted by either removing virtual objects from the scene or adding objects that have previously been removed responsive to the generated information.

Depending on the application, some virtual objects may be of higher priority than others. For example, a user playing a game may be more likely to interact with an avatar of another user 2210, 2220 than with a fixed object such as a tree 2230, 2240. The presence of an avatar 2210, 2220 in the virtual environment may be more important than the presence of a tree 2230, 2240 for the user's experience when playing a game, for example. A priority value can be associated with each virtual object in the image 2200 and the image can be adjusted to remove a virtual object 2230, 2240 with a low priority value responsive to the generated information indicating the well-being of the user. This provides an example of adjusting the number of virtual objects represented in the image 2200 based on a priority value associated with each virtual object in the image 2200.

Alternatively or in addition, the depth position of a virtual object and the priority value of that virtual object may be considered together so that a virtual object with a low priority value and a depth position near to the viewing point (such as the tree 2230) can be preferentially removed from the image 2200 before a virtual object with a low priority value and a depth position far away from the viewing point (such as the tree 2240). This means that a change in the information indicating the well-being of the user may mean that the tree 2230 is removed from the image 2200 while the tree 2240 is not removed, and a further change in the information may mean that the tree 2240 is subsequently removed from the image 2200. Similarly, a virtual object with a low priority value and a depth position far away from the viewing point (such as the tree 2240) can be preferentially removed from the image 2200 before a virtual object with a high priority value and a depth position far away from the viewing point (such as the avatar 2220). When simultaneously considering the depth position of a virtual object and the priority value of that virtual object, the box 2250 (with which the user may interact with) may have a higher priority value than the tree 2130, in which case the tree 2230 may be preferentially removed from the image 2200 before removing the box 2250 from the image.

Alternatively or in addition, the number of virtual objects in the image 2200 may be adjusted based on a geometric size of each virtual object in the image 2200 so that objects with a smaller geometric size can be preferentially removed from the image before larger objects. This means that the image 2200 can be adapted to remove objects in order of their size starting with the smallest objects and the adapted image may have fewer respective objects to allow the user to focus on fewer objects that are larger in size, which may be easier for the user to mentally anticipate. It will be appreciated that any combination of the depth position of each virtual object in the image 2200, the position of each virtual object in the image with respect to an avatar representation of the user or a viewpoint of the image 2200, the priority value of a virtual object in the image 2200, and the geometric size of a virtual object in the image 2200, may be simultaneously considered so that a virtual object can be removed from the image 2200.

It will be appreciated that the above techniques can similarly be applied so as to adjust the texture resolution of each respective virtual object in the image instead of adjusting the number of virtual objects in the image. The texture resolution of one or more of the virtual objects in the image can be adjusted according to the above techniques so that one or more of the virtual objects may be deemphasized with respect to other virtual objects in the virtual environment and the user's focus is more likely to be drawn away from these virtual objects.

It will be appreciated that the above techniques for adjusting the number of virtual objects in the image may be applied to adjust the transparency of each respective virtual object represented in the image instead of adjusting the number of virtual objects. In the above discussion a virtual object that is selected to be removed or added (a previously removed object may be added back in to the image responsive to the generated information) to the image may by rendered with a greater transparency instead of being removed, and the level of the transparency can be adjusted responsive to the generated information indicating the well-being of the user. This means that the virtual object can be rendered to be either completely transparent or with no transparency adjustment or anywhere between the two in accordance with the properties of the generated information.

In embodiments of the disclosure adapting the output of the HMD responsive to the generated information indicating the well-being of the user can comprise an adjustment of one or more from the list consisting of: a value associated with at least one of a plurality of component channels for pixels in the image output by the HMD; a frame rate of the image output by the HMD; and a volume of the audio signal output by the HMD.

The intensity of each of the red, green and blue component channels or the Y, U, V (luminance and chrominance) component channels of each pixel of the image may be adjusted responsive to the information indicating the well-being of the user by adjusting the binary values associated with each component channel. This means that the brightness of the image and/or the colour balance of the image output by the HMD can be adjusted responsive to the well-being of the user and visual fatigue that may be associated with the brightness and/or colour of the image may be inhibited. For example, the brightness of the image may be decreased by decreasing the binary values associated with each of the component channels when the information indicates deterioration in the well-being of the user, and the colour balance of the image may be adjusted by respectively scaling the red, green and blue (or the Y, U, V) component channels of the image to adjust the intensities of the respective colours in the image. Alternatively or in addition, the frame rate of the image can be adjusted responsive to the generated information by controlling the image generator to generate frames at a higher or lower rate based on the generated information. For example, a low frame rate (such as 30 fps) may mean that the displayed image does not correspond directly with what the user expected, and the frame rate may be increased responsive to the generated information so that the image displayed does not lag with respect to the image expected by the user. Alternatively or in addition, the blue light intensity of the image may be adjusted by adjusting the binary values associated with the blue component channel while the intensity of the red and green light of the image remains substantially the same, or the intensity of the blue component channel may be disproportionately adjusted when adjusting the intensity of the red, green and blue component channels. For example, the blue light intensity of the image may be either reduced or increased responsive to the generated information and the intensity of blue light can be reduced when the information indicates deterioration in the user's well-being. Alternatively or in addition, the volume (decibel rating) of the audio signal can be adjusted responsive to the generated information by adjusting a magnitude of the intensity of the audio signal.

In embodiments of the disclosure, in response to a change in a position or an orientation of a viewpoint of the image, the image can be adapted to adjust at least one of an acceleration and a velocity associated with the change in the position or the orientation of the viewpoint. The user wearing the HMD may move or rotate their head in a given direction, which causes a change in the position or the orientation of the viewpoint of the image so that a different portion of the virtual environment is displayed in the image output by the HMD. Consequently, the image output by the HMD can be adapted to change the viewpoint of the image in response to changes in the position and orientation of the user's head so that the rendered image may correspond with the user's physical movements.

Figure 23:
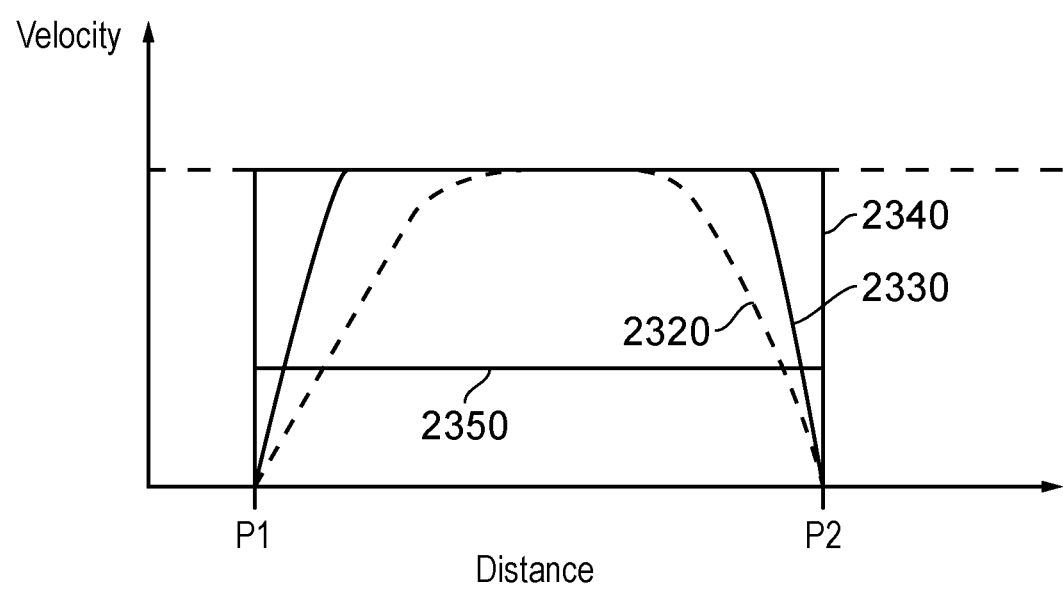
FIG. 23 schematically illustrates changing a viewpoint position from a first position to a second position with an adjusted acceleration.

FIG. 23 schematically illustrates changing a viewpoint position from a first position to a second position with an adjusted acceleration. The position of the viewpoint is changed from a first position P1 to a second position P2. Some user's may experience a conflict between the visual and vestibular systems when an acceleration of the viewpoint of the image occurs as the viewpoint is changed from the first position P1 to the second position P2 over a period of time. For example, as shown by the function 2320 (dashed line), an acceleration (positive acceleration) of the viewpoint may occur as the position of the viewpoint initially moves away from the first position P1 in a direction towards the second position P2, then an approximately constant velocity may be maintained for positions between the first and second positions, and an acceleration (negative acceleration) of the viewpoint may occur as the viewpoint approaches the second position P2. Note that function 2320 illustrates an example of a change in the position of the viewpoint of the image where the acceleration of the viewpoint is not adjusted, and this function serves as a reference.

Conflicts between the visual and vestibular systems of the user can either be prevented or the duration of these conflicts can be minimised by adjusting the acceleration or the velocity associated with the change in the position of the viewpoint when moving from the first position P1 to the second position P2. The image output by the HMD may be adapted responsive to the generated information and the acceleration associated with the change in the viewpoint position can be adjusted so that accelerations of the viewpoint are minimised in duration (shown by function 2330) or accelerations of the viewpoint are removed completely (shown by function 2340). When the acceleration is adjusted to remove any accelerations (function 2340), the viewpoint changes from the first position P1 to the second position P2 with a substantially constant velocity throughout the change in the position. This means that the magnitude of the acceleration associated with the change in the position of the viewpoint from P1 to P2 can be adjusted responsive to the information indicating the well-being of the user.

The acceleration associated with the change in the position of the viewpoint may be adjusted to remove or minimise the duration of any accelerations, and the magnitude of the substantially constant velocity at which the position of the viewpoint moves can be adjusted so that the viewpoint moves between P1 and P2 with a constant velocity that is less than or substantially the same as the constant velocity associated with function 2320, responsive to the information indicating the well-being of the user. Changing the position of the viewpoint from P1 to P2 with a smaller constant velocity means that the features in the virtual environment appear to move with a smaller velocity with respect to the viewpoint of the image. The magnitude of the constant velocity associated with the change in the position of the viewpoint from P1 to P2 can be adjusted responsive to the information indicating the well-being of the user.

Figure 24:
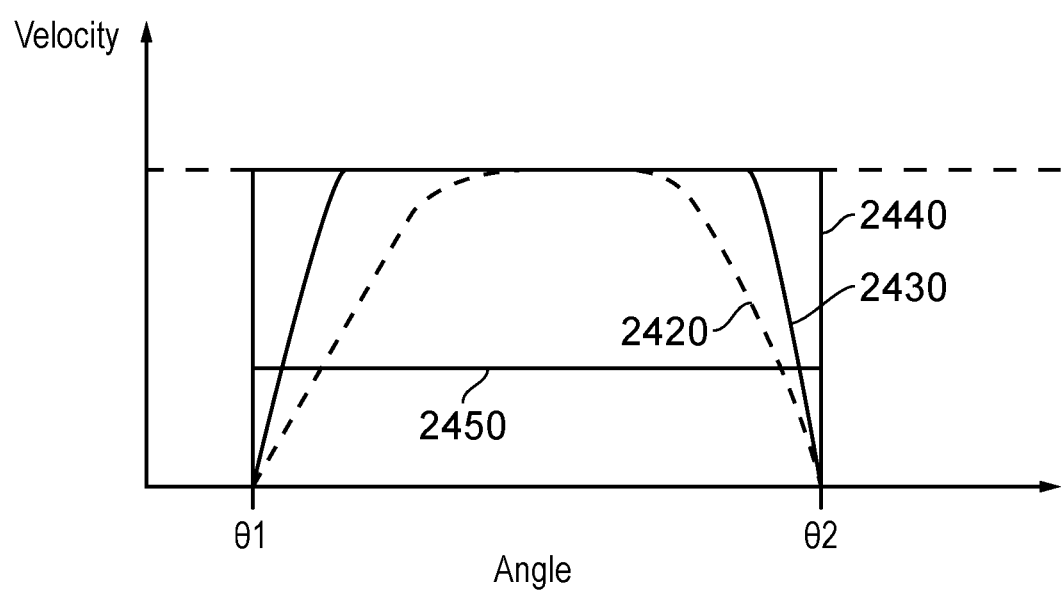
FIG. 24 schematically illustrates changing a viewpoint orientation from a first orientation to a second orientation with an adjusted acceleration and velocity.

FIG. 24 schematically illustrates changing a viewpoint orientation from a first orientation to a second orientation with an adjusted acceleration and velocity. The orientation of the viewpoint is changed from a first orientation $\theta1$ to a second orientation $\theta2$. A change in the orientation of the viewpoint of the image associated with a rotation of the user's head can also cause conflicts between the visual and vestibular systems of the user. For example, as shown by the function 2420 (dashed line), an acceleration (positive acceleration) of the viewpoint may occur as the orientation of the viewpoint initially rotates away from the first orientation $\theta1$ towards the second orientation $\theta2$, then an approximately constant velocity may be maintained between the first and second orientation, and an acceleration (negative acceleration) of the viewpoint may occur as the viewpoint approaches the second orientation $\theta2$. Note that function 2420 illustrates an example of a change in the orientation of the viewpoint of the image where the acceleration of the viewpoint is not adjusted, and this function serves as a reference.

Conflicts between the visual and vestibular systems of the user can either be prevented or the duration of these conflicts can be minimised by adjusting the acceleration associated with the change in the orientation of the viewpoint when moving from the first orientation $\theta1$ to the second orientation $\theta2$. The image output by the HMD may be adapted responsive to the generated information and the acceleration associated with the change in the viewpoint orientation can be adjusted so that accelerations of the viewpoint are minimised in duration (shown by function 2430) or accelerations of the viewpoint are removed completely (shown by function 2440). When the acceleration is adjusted to remove any accelerations (function 2440), the viewpoint changes from the first orientation $\theta1$ to the second orientation $\theta2$ with a substantially constant velocity throughout the change in the orientation. This means that the magnitude of the acceleration associated with the change in the orientation of the viewpoint from $\theta1$ to $\theta2$ can be adjusted responsive to the information indicating the well-being of the user.

The acceleration associated with the change in the orientation of the viewpoint may be adjusted to remove or minimise the duration of any accelerations, and the magnitude of the substantially constant velocity at which the orientation of the viewpoint rotates can be adjusted so that the viewpoint rotates between $\theta1$ and $\theta2$ with a constant velocity that is less than or substantially the same as the constant velocity associated with function 2420, responsive to the information indicating the well-being of the user. Changing the orientation of the viewpoint from $\theta1$ to $\theta2$ with a smaller constant velocity means that the features in the virtual environment appear to move with a smaller velocity with respect to the viewpoint of the image. The magnitude of the constant velocity associated with the change in the orientation of the viewpoint from $\theta1$ to $\theta2$ can be adjusted responsive to the information indicating the well-being of the user.

In embodiments of the disclosure, when the output of the HMD comprises a first audio signal, the output of the HMD can be adapted by selecting a second audio signal to be output by the HMD instead of the first audio signal. For example, the output of the HMD may comprise an image displaying visual content (e.g. a game) and a first audio signal associated with the visual content so that the user may hear sounds (such as a crash or a bang) that are related to the visual content. In accordance with the information indicating the well-being of the user, the output can be adapted so that the first audio signal is replaced with a second audio signal. For example, the second audio signal may differ from the first audio signal in that abrupt sounds related to the visual content in the image are not present in the second audio signal. Alternatively or in addition, a volume of the second audio signal may be lower than a volume of the first audio signal. The second audio signal output by the HMD instead of the first audio signal may comprise soothing audio.

In embodiments of the disclosure, an apparatus for updating content responsive to a well-being of a user 10 wearing an HMD 20 is provided. The apparatus comprises:

one or more sensors 1200 configured to detect one or more parameters indicating one or more current properties of the user 10 wearing the HMD 20;

a processor 300, 350, 20 configured to generate information indicating the well-being of the user 10 based on the one or more parameters;

an HMD 20 configured to output at least one of an image and an audio signal, the output adapted responsive to the generated information.

In embodiments of the disclosure, each of the one or more sensors 1200 of the apparatus is configured to communicate data indicative of the one or more parameters to the processor 300, 350, 20 via a wired or wireless communication means and the processor is configured to communicate data indicative of the generated information to the HMD 20 via a wired or wireless communication.

FIG. 25*a* schematically illustrates an apparatus for updating content responsive to a well-being of a user wearing an HMD, comprising an HMD and one or more sensors. The apparatus 2500 comprises one or more sensors 1200 that detect one or more parameters indicating one or more current properties of the user, and the one or more sensors can communicate data indicative of the one or more parameters to the processor of the HMD 20 via a wired or wireless communication. The one or more sensors 1200 may be provided as part of the HMD 20 or separate to the HMD 20 or a combination thereof, and the processor of the HMD 20 can be configured to generate the information indicating the well-being of the user based on the one or more parameters detected by the one or more sensors. The HMD 20 can then output at least one of an image and an audio signal that is adapted responsive to the information generated by the processor of the HMD 20.

FIG. 25*b* illustrates an apparatus for updating content responsive to a well-being of a user wearing an HMD comprising an HMD, one or more sensors, a computing device and an intermediate device. The apparatus 2500 comprises one or more sensors 1200 that may be provided as part of the HMD 20 or separate to the HMD 20 or a combination thereof. The one or more sensors may communicate data indicative of the one or more parameters to any of the HMD 20, the computing device 300 or the intermediate device 350. A processor of any of the HMD 20, the computing device 300 or the intermediate device 350 can generate information indicating the well-being of the user based on the one or more parameters detected by the one or more sensors. For example, a given sensor may detect one or more parameters and communicate data indicative of the one or more parameters to the HMD 20, the computing device 300 and the intermediate device 350 and processing tasks can be shared amongst the respective devices 20, 300, 350. The generated information indicating the well-being of the user can be communicated either via a wired or wireless communication link between respective devices 20, 300, 350 in order to share the generated information amongst the respective devices. The device responsible for generating the output of the HMD (for example, the image generator responsible for generating the image output by the HMD 20 may be part of the HMD 20 or may be part of the computing device 300) can thus be controlled responsive to the generated information and the HMD can be configured to output at least one of an image and an audio signal that is adapted responsive to the generated information.

In embodiments of the disclosure, the one or more sensors 1200 of the apparatus comprise one or more from the list consisting of: a temperature sensor 1210; a heart rate sensor 1220; an electrodermal activity sensor 1240; and an electroencephalography sensor 1270, configured to detect the one or more parameters indicating the one or more current properties comprising one or more physiological properties of the user.

In embodiments of the disclosure, the one or more sensors 1200 of the apparatus comprise at least one eye tracking camera 1230 configured to detect the one or more parameters indicating the one or more current properties comprising one or more physiological properties associated with at least one of the user's eyes.

In embodiments of the disclosure, the one or more sensors 1200 of the apparatus comprise at least one of a motion detector 1250 and a camera 1260 configured to detect the one or more parameters indicating the one or more current properties comprising at least one of an average motion of the user's head and an average motion of the user's body.

It will be apparent to a person skilled in the art that variations in the above method corresponding to operation of the various embodiments of the apparatus as described and claimed herein are considered within the scope of the present invention. It will be appreciated that example embodiments can be implemented by computer software operating on a general purpose computing system such as a games machine. In these examples, computer software, which when executed by a computer, causes the computer to carry out any of the methods discussed above is considered as an embodiment of the present disclosure. Similarly, embodiments of the disclosure are provided by a non-transitory, machine-readable storage medium which stores such computer software.

It will also be apparent that numerous modifications and variations of the present disclosure are possible in light of the above teachings. It is therefore to be understood that within the scope of the appended claims, the disclosure may be practised otherwise than as specifically described herein.

The invention claimed is:

1. A method of adapting content responsive to a well-being of a user wearing a head mountable display (HMD), the method comprising the steps of:
   detecting, by one or more sensors, one or more parameters indicating one or more current properties of the user wearing the HMD;
   generating information indicating the well-being of the user based on the one or more parameters; and
   adapting an output of the HMD responsive to the generated information, the output comprising at least one of an image and an audio signal,
   wherein the adapting step comprises adjusting either a number of virtual objects represented in the image or a texture resolution of each respective virtual object based on a priority value associated with each virtual object in the image.

2. The method according to claim 1, wherein the step of generating information comprises the step of:
   calculating, as part of the information, one or more respective well-being scores responsive to one or more of the detected parameters.

3. The method according to claim 2, wherein the step of generating information comprises the step of:
   calculating, as part of the information, a combined well-being score by combining one or more respective well-being scores.

4. The method according to claim 3, wherein the adapting step comprises providing a visual metric indicating the combined well-being score for the user.

5. The method according to claim 2, wherein the step of calculating the one or more respective well-being scores comprises comparing one or more of the detected parameters with one or more reference parameters.

6. The method according to claim 2, wherein the step of calculating the one or more respective well-being scores comprises comparing a rate of change of one or more of the detected parameters with one or more rate of change reference parameters.

7. The method according to claim 2, wherein adapting the image comprises providing a visual metric indicating one or more respective well-being scores for the user.

8. The method according to claim 1, wherein the one or more current properties of the user comprise one or more physiological properties from the list consisting of:
   a temperature of the user's body;
   a beating rate of the user's heart;
   a conductance of the user's skin; and
   an electrical activity of the user's brain.

9. The method according to claim 1, wherein the one or more current properties of the user comprise one or more physiological properties, associated with at least one of the user's eyes, from the list consisting of:
   a direction of the user's gaze;
   a pattern of the direction of the user's gaze;
   a dilation of at least one of the user's pupils;
   a pattern of the dilation of at least one of the user's pupils.

10. The method according to claim 1, wherein the one or more current properties of the user comprise at least one of an average motion of the user's head and an average motion of the user's body.

11. The method according to claim 1, wherein the adapting step comprises adjusting a field of view for the image.

12. The method according to claim 1, wherein the adapting step comprises adjusting a depth of field in the image.

13. The method according to claim 1, wherein the adapting step comprises adjusting either a number of virtual objects represented in the image or a texture resolution of each respective virtual object based on one or more from the list consisting of:
   a depth position of each virtual object in the image with respect to the viewpoint of the image;
   a geometric size of each virtual object in the image; and
   a position of each virtual object in the image with respect to either an avatar representation of the user or a viewpoint of the image.

14. The method according to claim 1, wherein the adapting step comprises adjusting one or more of the following:
   a value associated with at least one of a plurality of component channels for pixels in the image;
   a frame rate of the image; and
   a volume of the audio signal.

15. The method according to claim 1, wherein in response to a change in a position or an orientation of a viewpoint of the image, the adapting step comprises adjusting at least one of an acceleration and a velocity associated with the change in the position or the orientation of the viewpoint.

16. The method according to claim 1, wherein when the output of the HMD comprises a first audio signal, the adapting step comprises selecting a second audio signal to be output by the HMD instead of the first audio signal.

17. An apparatus for updating content responsive to a well-being of a user wearing a head mountable display (HMD), the apparatus comprising:
   one or more sensors configured to detect one or more parameters indicating one or more current properties of the user wearing the HMD;
   a processor configured to generate information indicating the well-being of the user based on the one or more parameters;
   an HMD configured to output at least one of an image and an audio signal, the output adapted responsive to the generated information to adjust either a number of virtual objects represented in the image or a texture resolution of each respective virtual object based on a priority value associated with each virtual object in the image.

18. The apparatus according to claim 17, wherein each of the one or more sensors is configured to communicate data indicative of the one or more parameters to the processor via a wired or a wireless communication means and the processor is configured to communicate data indicative of the generated information to the HMD via a wired or a wireless communication means.

19. The apparatus according to claim 17, wherein the one or more sensors comprise one or more from the list consisting of:
   a temperature sensor;
   a heart rate sensor;
   an electrodermal activity sensor; and
   an electroencephalography sensor, configured to detect the one or more parameters indicating the one or more current properties comprising one or more physiological properties of the user.

20. The apparatus according to claim 17, wherein the one or more sensors comprise at least one eye tracking camera configured to detect the one or more parameters indicating the one or more current properties comprising one or more physiological properties associated with at least one of the user's eyes.

21. The apparatus according to claim 17, wherein the one or more sensors comprise at least one of a motion detector and a camera configured to detect the one or more parameters indicating the one or more current properties comprising at least one of an average motion of the user's head and an average motion of the user's body.

22. A non-transitory, computer-readable storage medium containing computer software which, when executed by a computer, causes the computer to carry out a method of adapting content responsive to a well-being of a user wearing a head mountable display (HMD), by carrying out actions, comprising:
   detecting, by one or more sensors, one or more parameters indicating one or more current properties of the user wearing the HMD;
   generating information indicating the well-being of the user based on the one or more parameters; and
   adapting an output of the HMD responsive to the generated information, the output comprising at least one of an image and an audio signal,
   wherein the adapting step comprises adjusting either a number of virtual objects represented in the image or a texture resolution of each respective virtual object based on a priority value associated with each virtual object in the image.

* * * * *